US010130755B2

(12) United States Patent
Anderson et al.

(10) Patent No.: US 10,130,755 B2
(45) Date of Patent: Nov. 20, 2018

(54) DEVICES AND METHODS FOR DELIVERING A BENEFICIAL AGENT TO A USER

(71) Applicant: ABBVIE INC., North Chicago, IL (US)

(72) Inventors: Phil D. Anderson, Libertyville, IL (US); Kevin Novak, Park Ridge, IL (US); Gurjinder Dhami, Neenah, WI (US); Scott Smieja, Oshkosh, WI (US); Jeff Schacherl, Neenah, WI (US); Matthew Svacina, Brillion, WI (US)

(73) Assignee: ABBVIE INC., North Chicago, IL (US)

( * ) Notice: Subject to any disclaimer, the term of this patent is extended or adjusted under 35 U.S.C. 154(b) by 871 days.

(21) Appl. No.: 14/586,916

(22) Filed: Dec. 30, 2014

(65) Prior Publication Data
US 2015/0182689 A1 Jul. 2, 2015

Related U.S. Application Data

(60) Provisional application No. 62/054,153, filed on Sep. 23, 2014, provisional application No. 61/922,721, filed on Dec. 31, 2013.

(51) Int. Cl.
A61M 5/14 (2006.01)
A61M 5/142 (2006.01)

(52) U.S. Cl.
CPC ........ A61M 5/142 (2013.01); A61M 5/14228 (2013.01); A61M 5/14244 (2013.01);
(Continued)

(58) Field of Classification Search
CPC .............. A61M 5/142; A61M 5/14228; A61M 5/14244; A61M 2205/12; A61M 2205/121
See application file for complete search history.

(56) References Cited

U.S. PATENT DOCUMENTS 4,493,706 A 1/1985 Borsanyi et al.
4,537,561 A 8/1985 Xanthopoulos
(Continued)

FOREIGN PATENT DOCUMENTS

EP 1393762 A1 3/2004
JP 2005 351131 A 12/2005
JP 2005-351131 A 12/2005

OTHER PUBLICATIONS

U.S. Appl. No. 29/513,434, Jul. 20, 2015 Notice of Allowance.
(Continued)

Primary Examiner — Nathan R Price
Assistant Examiner — Courtney Fredrickson
(74) Attorney, Agent, or Firm — Baker Botts L.L.P.

(57) ABSTRACT

Device for delivering a beneficial agent includes a cassette including a cassette housing with a fluid reservoir and a cassette base region. The device also includes a delivery tube. The device also includes a pump including a pump housing containing a pump assembly having a fluid drive component. The pump housing has a receiving region to receive the cassette base region. The fluid drive component is proximate the receiving region. A lock member is coupled to the pump housing and movable between an open position and a closed position. The cassette is capable of being inserted into and removed from the receiving region when the lock member is in the open position, and the cassette is secured to the pump with the cassette base region within the receiving region and the delivery tube in operative engagement with the fluid drive component when the lock member is in the closed position.

20 Claims, 26 Drawing Sheets

(52) U.S. Cl.
CPC ... *A61M 2205/12* (2013.01); *A61M 2205/123* (2013.01); *A61M 2205/6027* (2013.01); *A61M 2205/6054* (2013.01); *A61M 2205/8206* (2013.01)

(56) References Cited

U.S. PATENT DOCUMENTS

| | | | |
|---|---|---|---|
| 5,131,816 | A | 7/1992 | Brown et al. |
| 5,181,910 | A | 1/1993 | Scanlon |
| D348,730 | S | 7/1994 | Walker et al. |
| 5,397,222 | A | 3/1995 | Moss et al. |
| 5,538,399 | A | 7/1996 | Johnson |
| D376,796 | S | 12/1996 | Hirasawa |
| 5,620,312 | A | 4/1997 | Hyman et al. |
| 5,718,562 | A | 2/1998 | Lawless et al. |
| 5,755,691 | A | 5/1998 | Hilborne |
| 5,928,196 | A | 7/1999 | Johnson et al. |
| 5,935,099 | A | 8/1999 | Peterson et al. |
| 6,077,055 | A | 6/2000 | Vilks |
| D439,341 | S | 3/2001 | Tumey et al. |
| 6,227,203 | B1 * | 5/2001 | Rise ............. A61M 5/14276 128/898 |
| 6,243,117 | B1 | 6/2001 | Brandon et al. |
| 6,305,908 | B1 | 10/2001 | Hermann et al. |
| 6,371,732 | B1 | 4/2002 | Moubayed et al. |
| 6,422,057 | B1 | 7/2002 | Anderson |
| D471,562 | S | 3/2003 | Kagami et al. |
| D471,917 | S | 3/2003 | Kagami et al. |
| D482,370 | S | 11/2003 | Niwatsukino et al. |
| D484,146 | S | 12/2003 | Urano et al. |
| 6,742,992 | B2 | 6/2004 | Davis |
| D517,091 | S | 3/2006 | Sugiyama et al. |
| 7,018,361 | B2 | 3/2006 | Gillespie, Jr. et al. |
| D520,023 | S | 5/2006 | Goto et al. |
| D520,024 | S | 5/2006 | Chen |
| D566,131 | S | 4/2008 | Detering et al. |
| D579,569 | S | 10/2008 | Strawn et al. |
| D583,856 | S | 12/2008 | Mizuno et al. |
| D585,543 | S | 1/2009 | Yodfat et al. |
| 7,628,770 | B2 | 12/2009 | Ethelfeld |
| D626,647 | S | 11/2010 | Amborn et al. |
| 7,927,306 | B2 | 4/2011 | Cross et al. |
| 8,114,066 | B2 | 2/2012 | Naef et al. |
| D655,810 | S | 3/2012 | Amborn et al. |
| D659,717 | S | 5/2012 | Mattson et al. |
| 8,298,184 | B2 | 10/2012 | DiPerna et al. |
| D675,252 | S | 1/2013 | Harvey et al. |
| 8,377,002 | B2 | 2/2013 | Hanson et al. |
| D687,140 | S | 7/2013 | Guarraia et al. |
| D689,523 | S | 9/2013 | Galbraith et al. |
| D697,204 | S | 1/2014 | Maier et al. |
| D720,804 | S | 1/2015 | Van Den Broecke |
| D725,678 | S | 3/2015 | Sekula et al. |
| 8,974,415 | B2 | 3/2015 | Robert et al. |
| D744,005 | S | 11/2015 | Anderson et al. |
| D744,586 | S | 12/2015 | Chung et al. |
| D746,441 | S | 12/2015 | Harr et al. |
| D746,871 | S | 1/2016 | Anderson et al. |
| D776,253 | S | 1/2017 | Li |
| 2003/0233069 | A1 | 12/2003 | Gillespie et al. |
| 2004/0051368 | A1 | 3/2004 | Caputo et al. |
| 2005/0094485 | A1 * | 5/2005 | Demers ............. A61L 2/0088 366/160.2 |
| 2007/0078377 | A1 | 4/2007 | Mason |
| 2008/0091139 | A1 | 4/2008 | Srinivasan et al. |
| 2008/0255516 | A1 | 10/2008 | Yodfat et al. |
| 2009/0182265 | A1 | 7/2009 | Mason |
| 2010/0049128 | A1 | 2/2010 | McKenzie et al. |
| 2010/0143168 | A1 | 6/2010 | Miyazaki et al. |
| 2011/0166511 | A1 | 7/2011 | Sharvit et al. |
| 2011/0202005 | A1 | 8/2011 | Yodfat et al. |
| 2011/0300010 | A1 * | 12/2011 | Jarnagin ............ A61B 17/3207 417/477.2 |
| 2012/0053522 | A1 | 3/2012 | Yodfat et al. |
| 2012/0191059 | A1 | 7/2012 | Cummings et al. |
| 2012/0217276 | A1 * | 8/2012 | Kennedy ............. B60R 11/06 224/400 |
| 2012/0277667 | A1 | 11/2012 | Yodat et al. |
| 2013/0154252 | A1 | 6/2013 | Rakowicz et al. |
| 2013/0267899 | A1 | 10/2013 | Robert et al. |
| 2014/0194818 | A1 | 7/2014 | Yodfat et al. |

OTHER PUBLICATIONS

U.S. Appl. No. 29/513,434, Oct. 20, 2015 Issue Fee Payment.
U.S. Appl. No. 29/513,436, Aug. 24, 2015 Notice of Allowance.
U.S. Appl. No. 15/064,481, filed Mar. 8, 2016.
U.S. Appl. No. 29/550,455, filed Jan. 4, 2016.
U.S. Appl. No. 29/513,436, Nov. 24, 2015 Issue Fee Payment.
U.S. Appl. No. 29/513,438, Feb. 26, 2016 Notice of Allowance.
U.S. Appl. No. 29/513,435, May 19, 2016 Non-Final Office Action.
U.S. Appl. No. 29/513,437, May 20, 2016 Non-Final Office Action.
U.S. Appl. No. 29/566,784, filed Jun. 2, 2016.
U.S. Appl. No. 29/513,435, Aug. 18, 2016 Response to Non-Final Office Action.
U.S. Appl. No. 29/513,437, Sep. 9, 2016 Notice of Allowance.
U.S. Appl. No. 29/513,437, Aug. 18, 2016 Response to Non-Final Office Action.
U.S. Appl. No. 29/513,438, Jun. 28, 2016 Notice of Allowance.
U.S. Appl. No. 29/513,438, May 26, 2016 Notice of Allowance.
U.S. Appl. No. 29/513,438, May 26, 2016 Issue Fee Payment.
International Search Report and Written Opinion dated Mar. 30, 2015 in International Application No. PCT/US2014/072973.
International Search Report and Written Opinion dated Mar. 30, 2015 in International Application No. PCT/US2014/072979.
U.S. Appl. No. 29/513,435, Sep. 15, 2016 Notice of Allowance.
U.S. Appl. No. 29/566,784, Sep. 16, 2016 Notice of Allowance.
U.S. Appl. No. 29/513,434, filed Dec. 30, 2014.
U.S. Appl. No. 29/513,435, filed Dec. 30, 2014.
U.S. Appl. No. 29/513,436, filed Dec. 30, 2014.
U.S. Appl. No. 29/513,437, filed Dec. 30, 2014.
U.S. Appl. No. 29/513,438, filed Dec. 30, 2014.
U.S. Appl. No. 14/586,912, filed Dec. 30, 2014.
U.S. Appl. No. 14/586,912, Nov. 24, 2017 Non-Final Office Action.
U.S. Appl. No. 29/513,435, Dec. 14, 2016 Issue Fee Payment.
U.S. Appl. No. 29/513,437, Dec. 8, 2016 Issue Fee Payment.
U.S. Appl. No. 29/550,455, Dec. 6, 2017 Notice of Allowance.
U.S. Appl. No. 29/550,455, Nov. 2, 2017 Issue Fee Payment.
U.S. Appl. No. 29/550,455, Oct. 27, 2017 Notice of Allowance.
U.S. Appl. No. 29/550,455, Aug. 3, 2017 Notice of Allowance.
U.S. Appl. No. 29/566,784, Dec. 15, 2016 Issue Fee Payment.
U.S. Appl. No. 29/566,784, Dec. 7, 2016 Notice of Allowance.
U.S. Appl. No. 29/566,784, Nov. 2, 2016 Notice of Allowance.
U.S. Appl. No. 15/064,481, May 17, 2018 Non-Final Office Action.

* cited by examiner

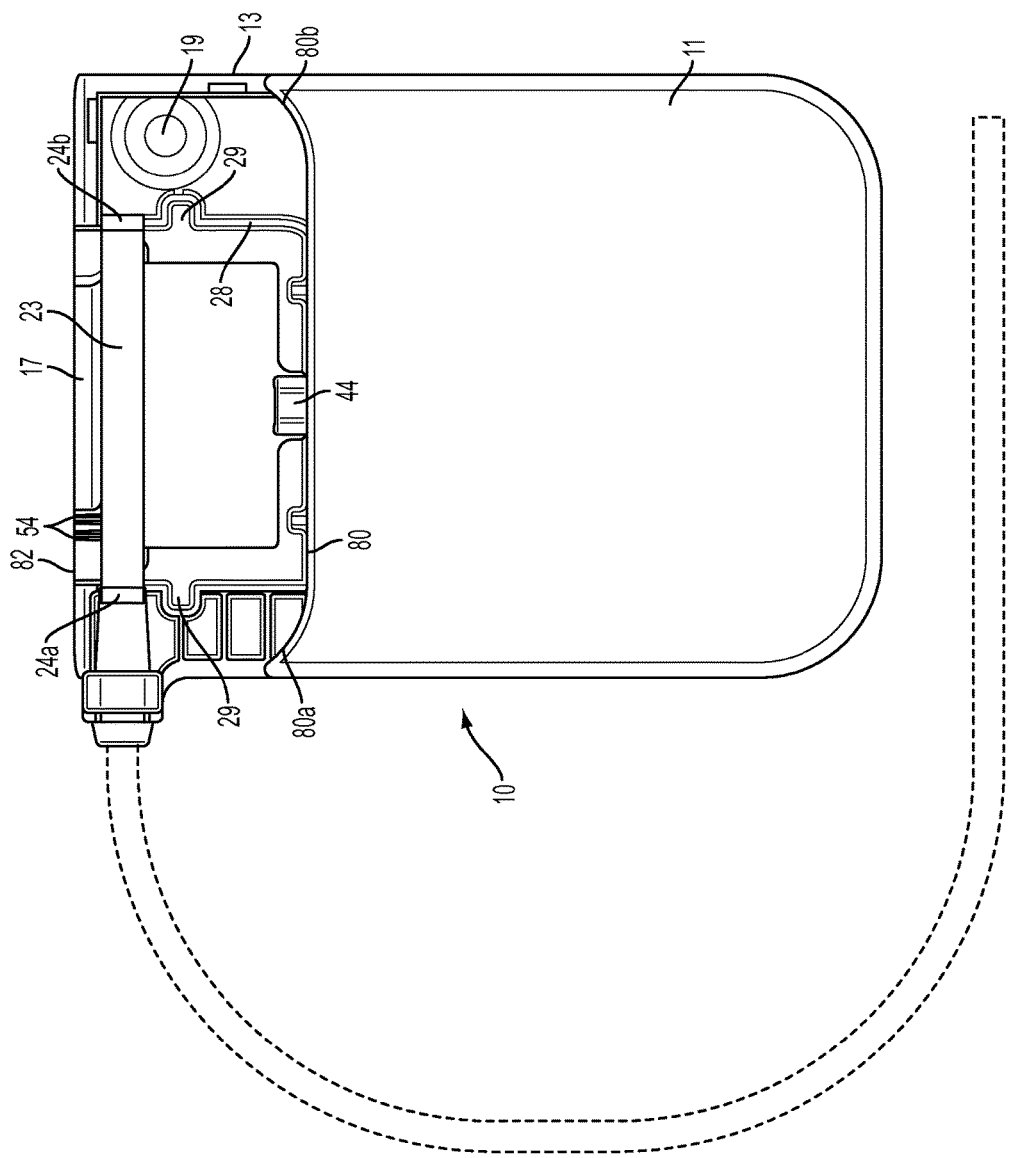

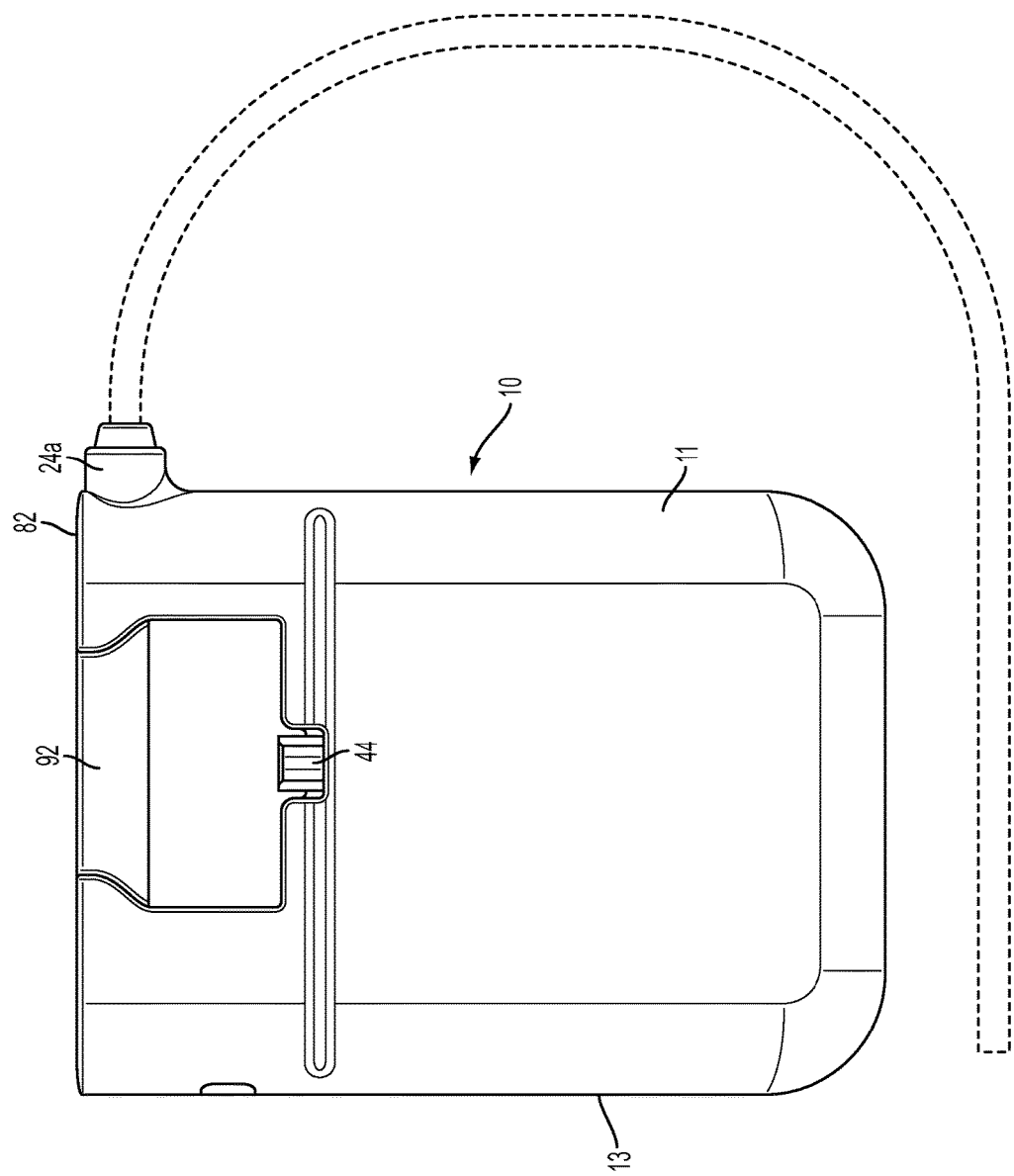

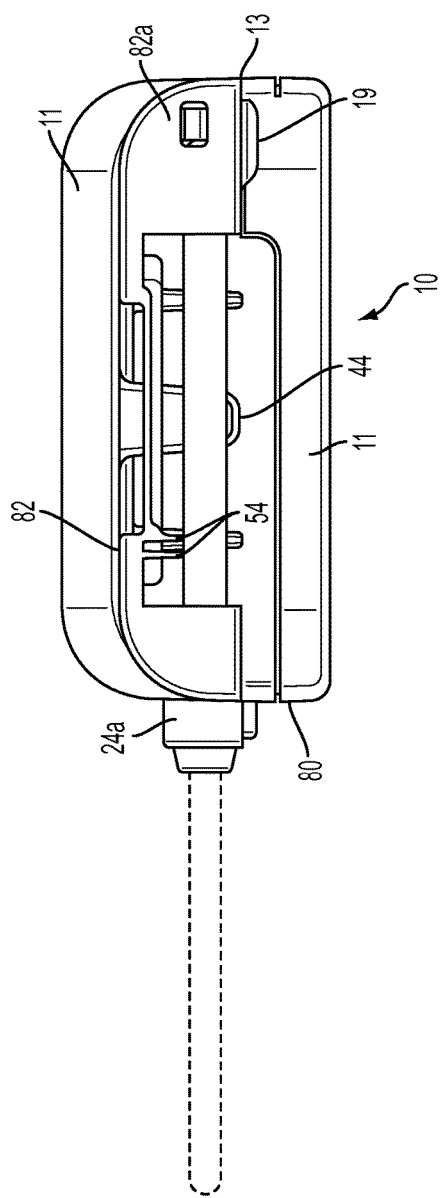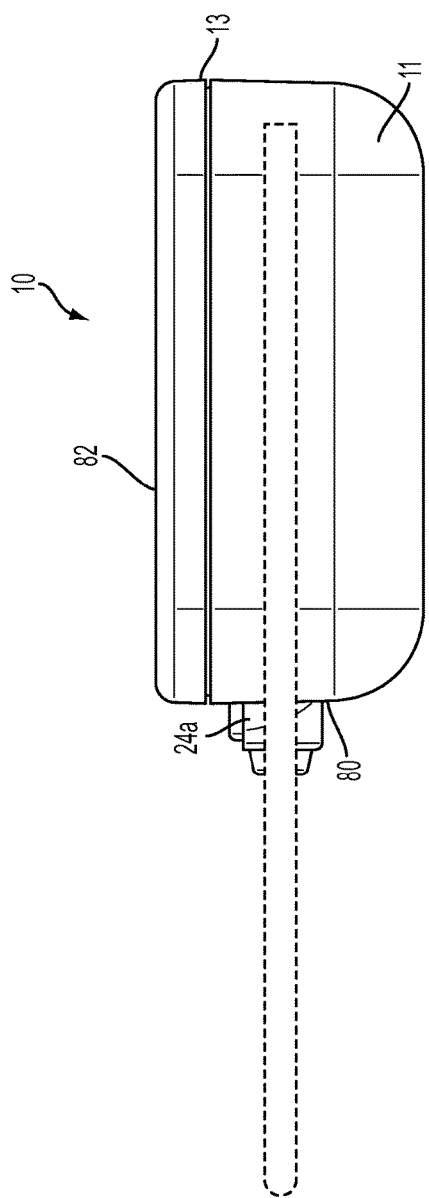

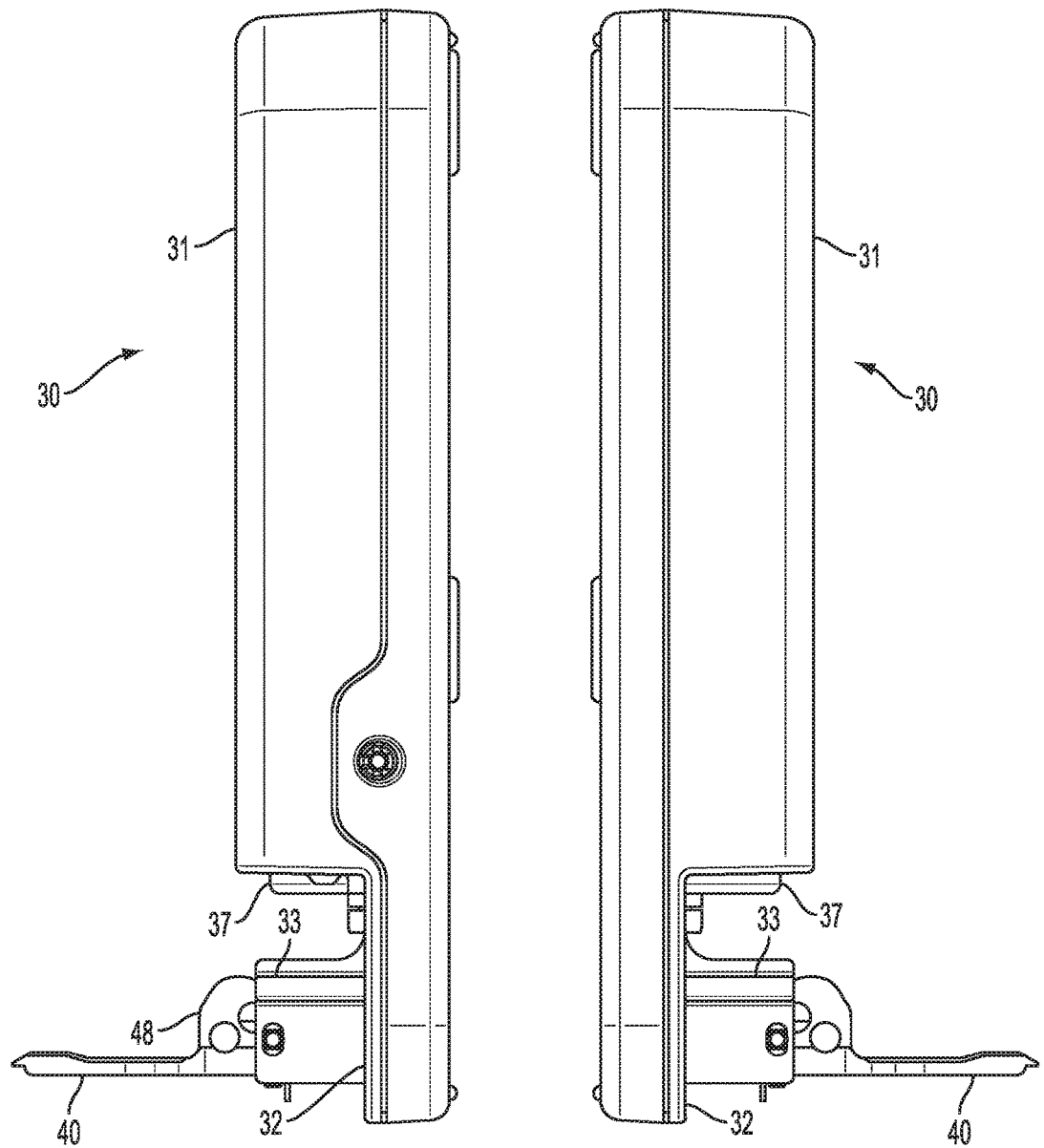

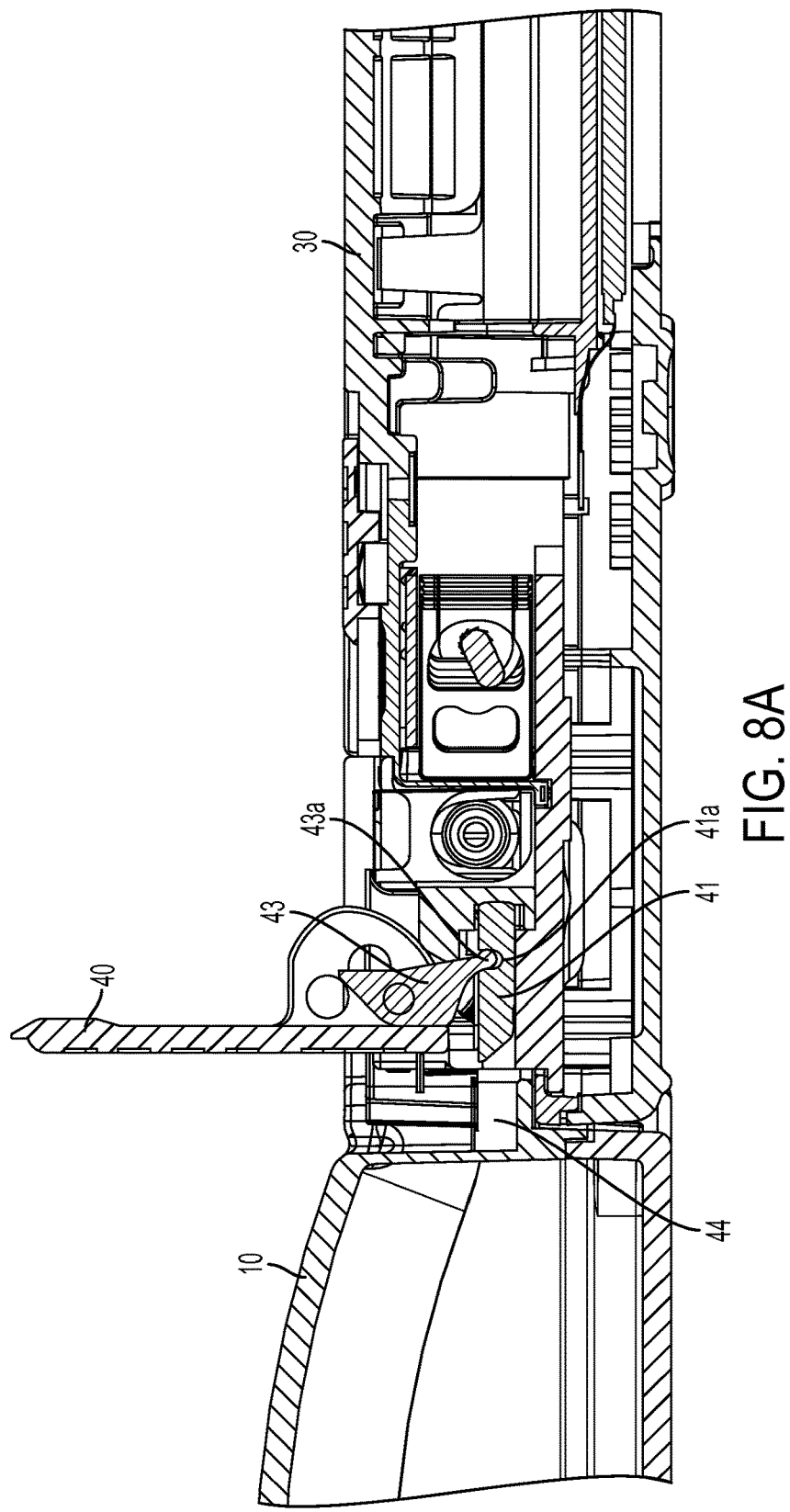

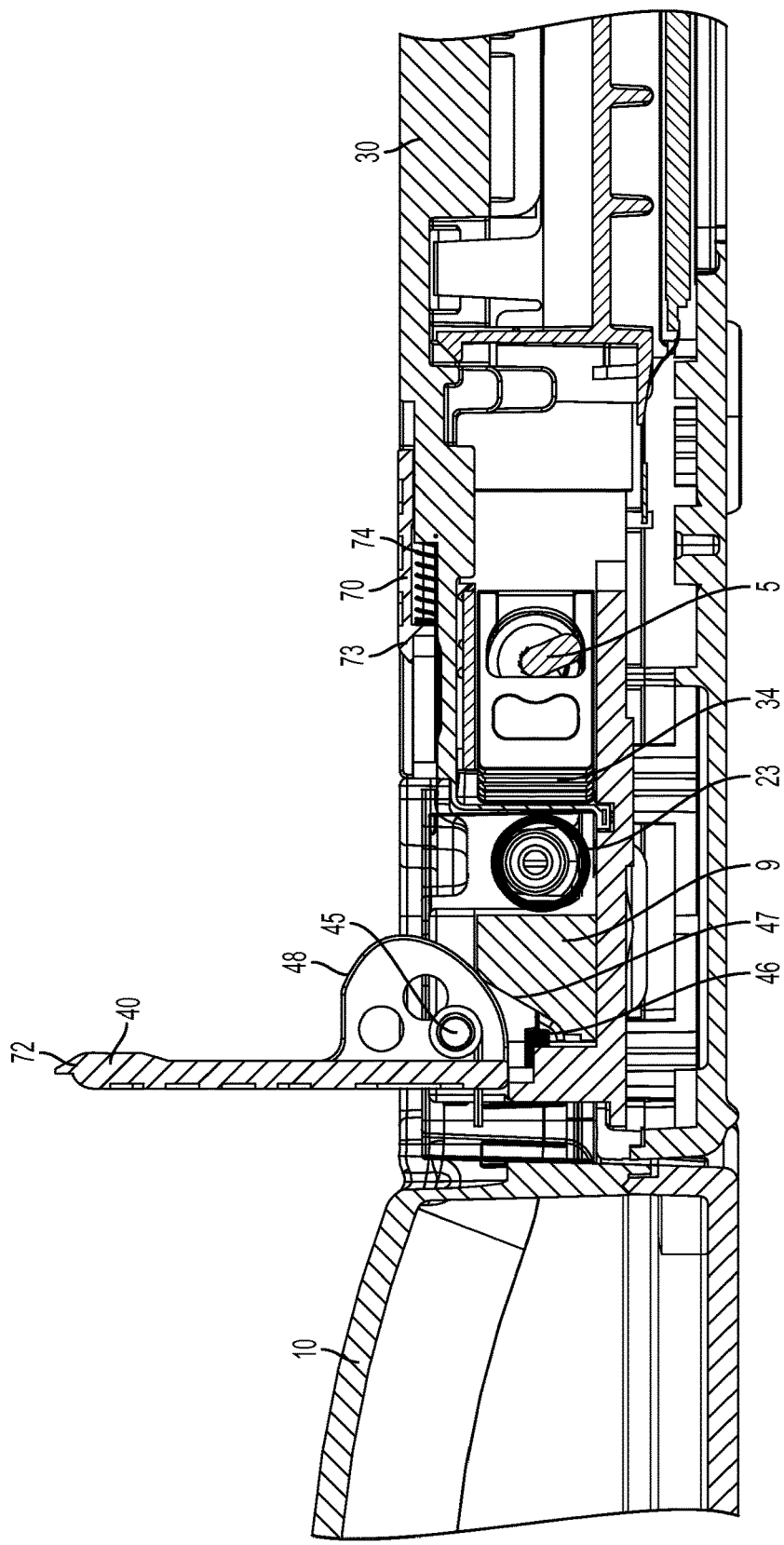

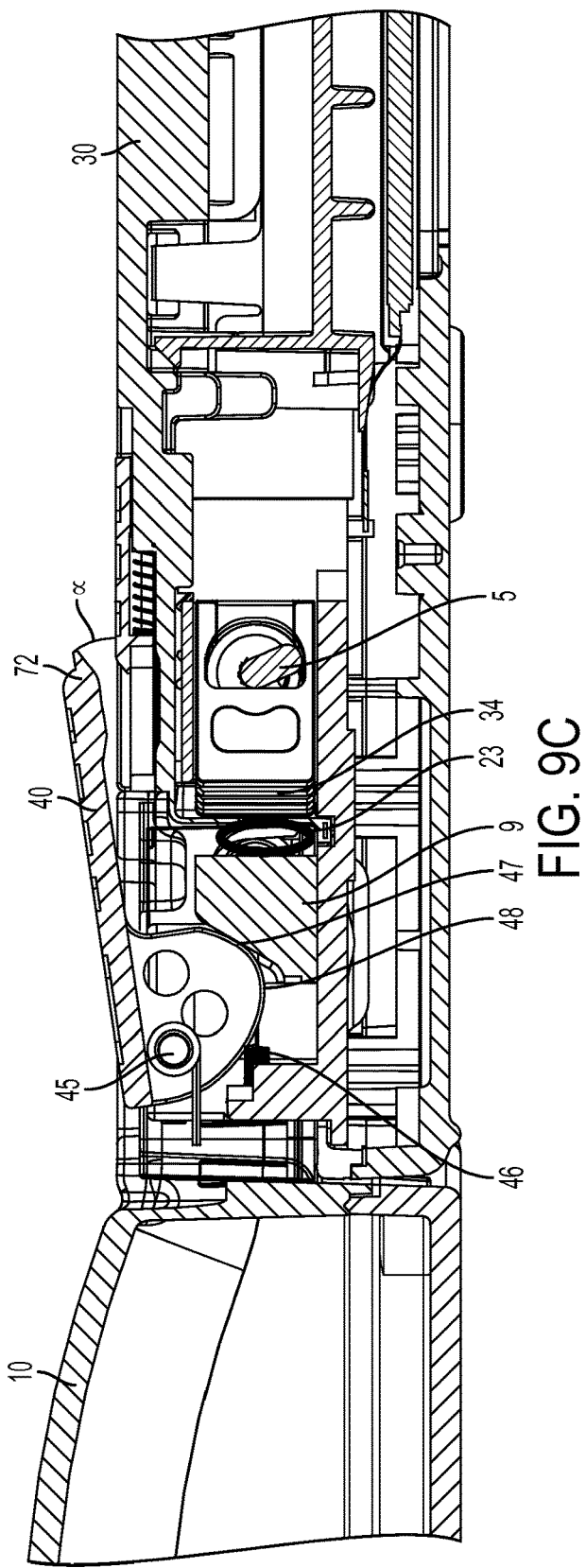

DEVICES AND METHODS FOR DELIVERING A BENEFICIAL AGENT TO A USER

CROSS-REFERENCE TO RELATED APPLICATIONS

This application claims priority to U.S. Provisional Patent Application Nos. 61/922,721, filed Dec. 31, 2013; and 62/054,153, filed Sep. 23, 2014; each of which is incorporated by reference herein in its entirety.

BACKGROUND

Field of the Disclosed Subject Matter

The disclosed subject matter relates to devices, systems and methods for controlling and delivering fluids, for example for delivery of a beneficial agent to a user.

Description of Related Art

A variety of fluid transport devices and systems have been developed for controlling and delivering beneficial agents in fluid form. Such fluid flow systems can include 1) volumetric-based aspiration flow systems using positive displacement pumps, and 2) vacuum-based aspiration systems using a vacuum source. For example, volumetric aspiration systems include peristaltic pumps for the delivery of therapeutic agents to a user. Various forms of peristaltic pumps are known, such as using rotating rollers to press against a flexible tubing to induce flow therethrough. Cassette systems or other reservoir configurations can be coupled with the pump to provide a source of beneficial agent fluid via the flexible tubing.

Such devices and systems are particularly beneficial as portable infusion pumps capable of being worn or carried by the user. However, there remains a need for improvement of such devices and systems. Such improvements include, among other things, improved energy consumption and battery life, improved pump efficiency and control, improved comfort and ergonomics, and improved cassette configuration for more complete access to the reservoir contents.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a drug delivery reservoir cassette for a pump, the pump having a lock member movable between an open position and a closed position. The cassette generally includes a cassette housing including a cassette body region and a cassette base region. The cassette housing has a front surface, a back surface and lateral sidewalls. The cassette housing defines a transverse axis extending between the lateral sidewalls and a longitudinal axis perpendicular to the transverse axis. The cassette body region defines a fluid reservoir chamber therein. As embodied herein, for purpose of illustration and not limitation, the cassette base region can be disposed along the longitudinal axis from the cassette body region. The cassette base region has a boundary configured to be received by the pump. As disclosed herein, the cassette base region can include one or more features, alone or in combination, to align and secure the cassette when received by the pump.

In accordance with one aspect of the disclosed cassette base region, the boundary can include a pair of opposing rails disposed on opposite sides of the longitudinal axis. As embodied herein, the pair of opposing rails can be substantially symmetrical about the longitudinal axis. Each of the opposing rails can be recessed relative an adjacent portion of the boundary. The pair of opposing rails can be aligned along a transverse axis relative the longitudinal axis. Each of opposing rails can define an abutment surface generally parallel with the transverse axis.

Furthermore, and as embodied herein, the cassette base region can include an engagement surface configured to be engaged by the lock member when in the closed position. The pair of rails can be spaced from the engagement surface in a direction along the longitudinal axis. The boundary can also include an alignment key aligned parallel with the longitudinal axis and can define a receiving recess to receive an alignment pin from the pump. The alignment key can be spaced from the pair of rails and from the engagement surface in a direction along the longitudinal axis. The cassette can further include a delivery tube assembly extending from the fluid reservoir chamber, and the cassette base region can include a support rib projecting from the boundary in engagement with the delivery tube. The cassette base region can include a flat surface proximate an end of the cassette housing. The flat surface can include two flat surface portions. Additionally or alternatively, the cassette base region can include a contoured surface configured to mate a corresponding surface of the pump. For example, the contoured surface can have a concave shape directed toward the boundary in plan view. The contoured surface can be substantially symmetrical about the longitudinal axis.

According to another aspect of the disclosed cassette, the cassette base region can include an engagement surface configured to be engaged by the lock member when in the closed position. The engagement surface can be substantially coplanar with the back surface of the cassette housing. Alternatively, the engagement surface can include a recessed area recessed relative the back surface of the cassette base region. The recessed area can be shaped to receive the lock member when in the closed position. As embodied herein, the recessed area can taper to a reduced or smaller cross dimension in plan view toward an end of the cassette housing.

Furthermore, and as embodied herein, the engagement surface can include a pair of engagement surface portions on opposite sides of the longitudinal axis. The pair of engagement surface portions can be substantially symmetrical about the longitudinal axis. The engagement surface can include an elongated strip. The engagement surface can include a unitary bridge across the longitudinal axis. Additional features of the cassette as disclosed herein can be combined with the engagement surface of this aspect.

According to another aspect of the disclosed cassette as set forth above, the cassette base region can include an alignment key aligned parallel with the longitudinal axis and defining a receiving recess to receive an alignment pin from the pump. The alignment key can be centered between the lateral side walls. The alignment key can project from the cassette body region into the cassette base region, and particularly, the alignment key can project into the boundary. The alignment key can be channel-shaped to define the receiving recess. Additionally or alternatively, the receiving recess can be tapered along the longitudinal axis. Additional features of the cassette as disclosed herein can be combined with the alignment key of this aspect.

According to another aspect of the disclosed cassette as set forth above, a delivery tube assembly can be provided extending from the fluid reservoir chamber. The cassette base region can include a support rib projecting from the boundary in engagement with the delivery tube. The support rib can include a pair of support rib portions. The delivery tube assembly can include a pair of end fittings to receive a peristaltic tube, and the support rib can be substantially aligned between the pair of end fittings. Additional features of the cassette as disclosed herein can be combined with the support rib of this aspect.

According to another aspect of the disclosed subject matter, a device for delivering a beneficial agent is provided. The device generally includes a pump and a cassette. The pump includes a pump housing containing a pump assembly having a fluid drive component. The pump housing has a receiving region disposed proximate the fluid drive component. The cassette can include any combination of features described herein.

According to another aspect of the disclosed subject matter, and further to the above, a device for delivering a beneficial agent is provided. The device generally includes a cassette, a pump, a delivery tube and a lock member. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component. The pump housing has a receiving region to receive the cassette base region. The fluid drive component is disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region and a length of the delivery tube in operative engagement with the fluid drive component when the lock member is in the closed position.

Additionally, and as embodied herein, an alignment pin can be operatively coupled to the lock member. Movement of the lock member between the open position and the closed position can extend at least a portion of the alignment pin into engagement with the cassette housing. The cassette housing can define a receiving recess proximate the cassette base region to receive the alignment pin when the lock member is moved toward the closed position. The receiving recess can be tapered toward a closed end. The receiving recess can be defined by an alignment key projecting from the cassette body region into the cassette base region. For example, the cassette base region can include an alignment key having a receiving recess to receive the alignment pin. The alignment pin can include a tapered end. The lock member can include a protrusion, and the alignment pin can include a notch to receive the protrusion to engage the lock member to operatively couple the alignment pin to the lock member.

Furthermore, and as embodied herein, the lock member can include a latch, which can be configured as a cam lever. The receiving region can further include a torsion spring mechanically coupled to the latch to bias the latch toward the open position.

In addition, and as embodied herein, the latch can further include a latch cam surface, and the pump can further include an occlusion block disposed proximate the receiving region and having an occlusion block cam surface. The occlusion block can be biased to urge the occlusion block cam surface against the latch cam surface. The latch cam surface and the occlusion block cam surface can be configured to urge the occlusion block toward an operative position to hold the peristaltic tube in functional relationship to the fluid drive component when the latch is moved from the open position toward the closed position. The latch cam surface and the occlusion block cam surface can be configured to define a dead zone where the occlusion block remains in the operative position during continued movement of the latch continues from the open position to the closed position. For example, the dead zone can be defined by 10 degrees of final movement of the latch from the open position to the closed position with no corresponding movement of the occlusion block. The latch can include a pivotal latch mounted on a hinge. Alternatively, the latch can include a draw latch mounted for sliding movement.

According to another aspect of the disclosed subject matter, and further to the above, a device for delivering a beneficial agent is provided. The device generally includes a cassette, a pump, a delivery tube and a lock member. The cassette includes a cassette housing with a fluid reservoir defined therein. The cassette housing has a cassette base region, and the cassette base region includes a radio frequency identification (RFID) shell housing a RFID tag. The delivery tube is fluidly coupled with the fluid reservoir. The pump includes a pump housing containing a RFID reader and a pump assembly having a fluid drive component. The pump housing has a receiving region to receive the cassette base region. The RFID reader and the fluid drive component are disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region with the RFID tag disposed proximate the RFID reader and a length of the delivery tube in operative engagement with the fluid drive component when the lock member is in the closed position.

Additionally, and as embodied herein, the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent.

Furthermore, and as embodied herein, the receiving region can further include a RFID receiving region with the RFID reader housed therein. The RFID receiving region can be configured to engage the RFID shell when the cassette is secured to the pump with the cassette base region within the receiving region of the pump housing. The RFID receiving region can have a shape configured to mate with the RFID shell. For example, the RFID shell can include a raised surface relative an adjacent surface of the cassette base region, and the RFID receiving region can include a dimple configured to receive the raised surface when the cassette is secured to the pump with the cassette base region within the receiving region of the pump housing. The RFID shell and RFID receiving region can be configured to dispose the RFID tag within about 5 mm of the RFID reader when the cassette is secured to the pump with the cassette base region within the receiving region of the pump housing. The RFID reader can have a range of detection configured to read the RFID tag only when the RFID receiving region is in engagement with the RFID shell. The device can further include a processor coupled to the RFID reader and configured to verify identification information for the cassette encoded on the RFID tag. Additionally or alternatively, the processor can be coupled to the RFID reader and configured to enable operation of the pump if an expiration date of the beneficial agent encoded on the RFID tag is not exceeded. In addition or as a further alternative, the processor can be coupled to the RFID reader and configured to determine one or more dosing options based at least in part on a concentration of the beneficial agent encoded on the RFID tag. The RFID tag can include high or ultra-high radio frequency ID.

According to another aspect of the disclosed subject matter, and further to the above, a drug delivery reservoir cassette for a pump having an RFID reader, a receiving region configured to receive the cassette, and a lock member movable between an open position and a closed position is provided. The cassette includes a cassette housing with a fluid reservoir defined therein. The cassette housing has a cassette base region. The cassette base region includes a radio frequency identification (RFID) shell housing a RFID tag configured to be read by the RFID reader. The cassette is capable of being inserted into and removed from the receiving region when the lock member is in the open position, and the cassette is secured to the pump with the cassette base region within the receiving region with the RFID tag disposed proximate the RFID reader when the lock member is in the closed position.

The cassette can include any combination of features described herein. For example, and as embodied herein, the RFID shell comprises a raised surface relative an adjacent surface of the cassette base region. the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent.

As embodied herein, any of the various devices and cassette can include a beneficial agent contained in the fluid reservoir. The beneficial agent can include one or more of levodopa and carbidopa.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIGS. 4A-4G are perspective, front, rear, left side, right side, top and bottom views, respectively, of an exemplary cassette of the device of FIG. 1.

FIGS. 5A-5G are perspective, front, rear, left side, right side, top and bottom views, respectively, of an exemplary pump of the device of FIG. 1.

FIG. 8A is a cross-sectional view of the exemplary device taken along line 8A-8A of FIG. 2.

FIG. 9A is a cross-sectional view of the exemplary device taken along line 9A-9A of FIG. 2.

FIG. 9C is a cross-sectional view of the exemplary device of FIG. 9A, with the lock member urged further from the open position toward the closed position.

DESCRIPTION

Figure 1:
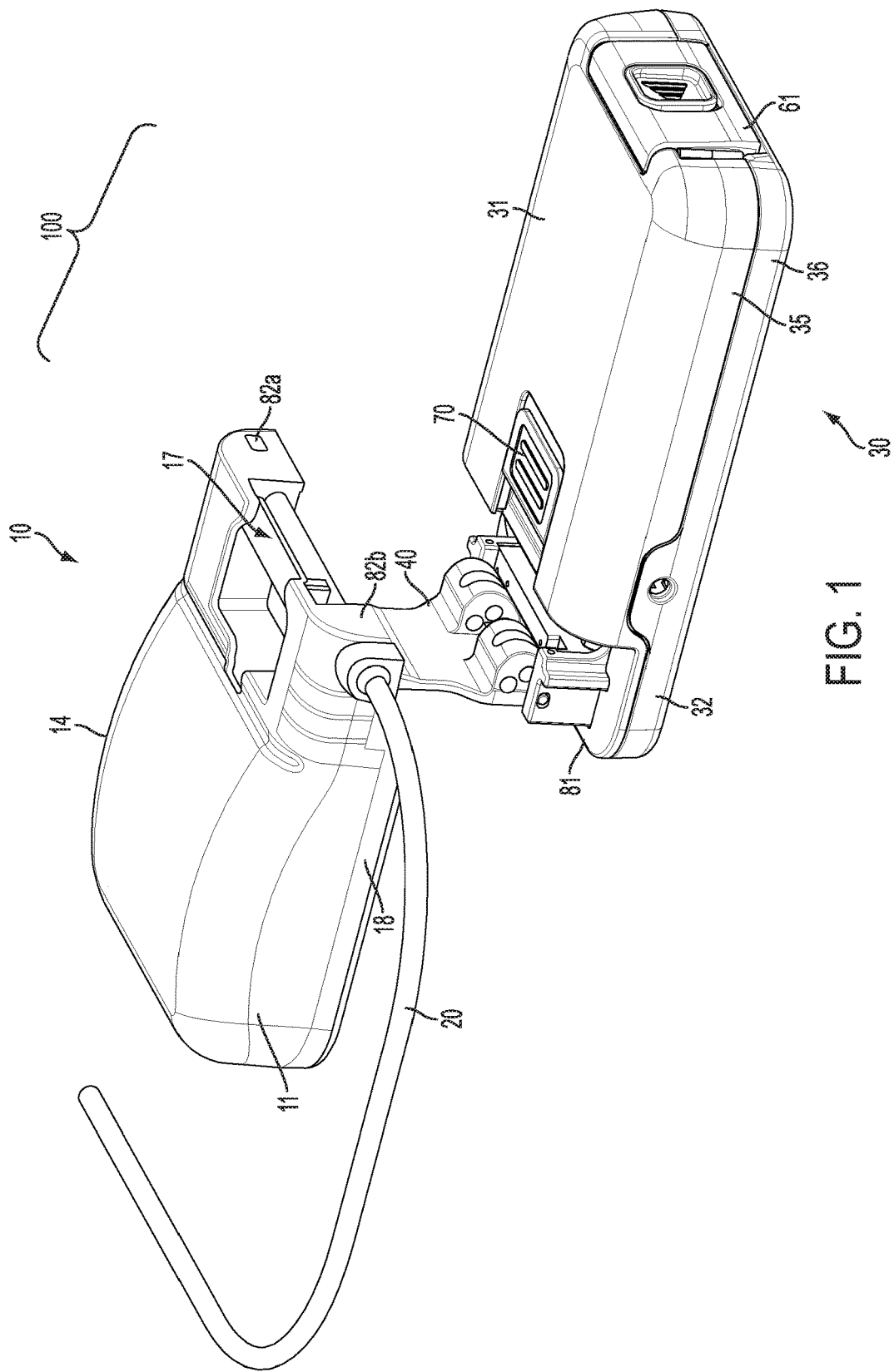
FIG. 1 is an exploded perspective view of an exemplary device for delivering a beneficial agent according to the disclosed subject matter.

Reference will now be made in detail to the various exemplary embodiments of the disclosed subject matter, exemplary embodiments of which are illustrated in the accompanying drawings. The structure and corresponding method of operation of and method of using the disclosed subject matter will be described in conjunction with the detailed description of the system.

The apparatus and methods presented herein can be used for administering any of a variety of suitable therapeutic agents or substances, such as a drug or biologic agent, to a patient. For example, and as embodied herein, the device can include a pump joined to a cassette, which can include a fluid reservoir containing a fluid substance and can be joined to a delivery tube system. In operation, the pump can operate on the cassette to deliver the fluid substance through the tubing system. In this manner, the device is capable of administering a dosage of the fluid substance, such as a therapeutic agent, including a formulation in a liquid or gel form, through the delivery tube system and to a patient. In some embodiments, the fluid therapeutic agent can include one or more pharmaceutical or biologic agents. For example and without limitation, one such fluid therapeutic agent can be a central nervous system agent, such as levodopa. The central nervous system agent can be administered alone or in combination with, for example and without limitation, a decarboxylase inhibitor, such as carbidopa.

In accordance with one aspect of the disclosed subject matter, a drug delivery reservoir cassette for a pump is provided. The pump has a lock member movable between an open position and a closed position, such as described further below. The cassette generally includes a cassette housing including a cassette body region and a cassette base region. The cassette housing has a front surface, a back surface and lateral sidewalls. The cassette housing defines a transverse axis extending between the lateral sidewalls and a longitudinal axis perpendicular to the transverse axis. The cassette body region defines a fluid reservoir chamber therein. As embodied herein, for purpose of illustration and not limitation, the cassette base region can be disposed along the longitudinal axis from the cassette body region. The cassette base region has a boundary configured to be received by the pump. The cassette base region can include one or more features as described herein for alignment and securement of the cassette when received by the pump.

As embodied herein, the boundary can include a pair of opposing rails disposed on opposite sides of the longitudinal axis. For example, the pair of opposing rails can be substantially symmetrical about the longitudinal axis. Each of the opposing rails can be recessed relative an adjacent portion of the boundary. The pair of opposing rails can be aligned along a transverse axis relative the longitudinal axis. Each of opposing rails can define an abutment surface generally parallel with the transverse axis.

Additionally or alternatively, or in combination with any of the features of the cassette base region described herein, the cassette base region can include an engagement surface configured to be engaged by the lock member when in the closed position. For example, the pair of rails can be spaced from the engagement surface in a direction along the longitudinal axis, if combined together. As embodied herein, the engagement surface can be substantially coplanar with the back surface of the cassette housing. Alternatively, the engagement surface can include a recessed area recessed relative the back surface of the cassette base region. The recessed area can be shaped to receive the lock member when in the closed position. As embodied herein, the recessed area can taper to a reduced or smaller dimension in plan view toward an end of the cassette housing.

Additionally or alternatively, or in combination with any of the features of the cassette base region described herein, the boundary can include an alignment key aligned parallel with the longitudinal axis and defining a receiving recess to receive an alignment pin from the pump. As embodied herein, the alignment key can be centered between the lateral side walls. The alignment key can project into the boundary. The alignment key can project from the cassette body region into the cassette base region. The alignment key can be channel-shaped. Additionally or alternatively, the receiving recess can be tapered along the longitudinal axis.

Additionally or alternatively, or in combination with any of the features of the cassette base region described herein, the cassette can include a delivery tube assembly extending from the fluid reservoir chamber, and the cassette base region can include a support rib projecting from the boundary in engagement with the delivery tube. As embodied herein, the support rib can include a pair of support rib portions. The delivery tube assembly can include a pair of end fittings to receive a peristaltic tube, and the support rib can be substantially aligned between the pair of end fittings.

Additionally or alternatively, or in combination with any of the features of the cassette base region described herein, the cassette base region can include a flat surface proximate an end of the cassette housing. The flat surface can include two flat surface portions.

Additionally or alternatively, or in combination with any of the features of the cassette base region described herein, the cassette base region can include a contoured surface configured to mate with a corresponding surface of the pump. The contoured surface can have a concave shape directed toward the boundary in plan view. The contoured surface can be substantially symmetrical about the longitudinal axis.

According to another aspect of the disclosed subject matter, and further to the above, a device for delivering a beneficial agent is provided. The device generally includes a pump and a cassette. The pump includes a pump housing containing a pump assembly having a fluid drive component. The pump housing has a receiving region disposed proximate the fluid drive component, the receiving region configured to receive at least a portion of the cassette. The cassette can include any combination of features of the cassette base region described herein.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the device for delivering a beneficial agent, including a drug delivery reservoir cassette, in accordance with the disclosed subject matter are shown in FIGS. 1-13.

While the disclosed subject matter is described with respect to a delivery device to administer a dose of therapeutic agent, one skilled in the art will recognize that the disclosed subject matter is not limited to the illustrative embodiment, and that the devices disclosed herein can be configured for delivering any suitable substance therethrough. In addition, the components and the method of using the delivery device are not limited to the illustrative embodiments described or depicted herein. For example, the delivery device embodied herein can be used with other tubing assemblies and components thereof for similar benefits and advantages, and are not limited for use with the delivery tubing herein.

Figure 2:
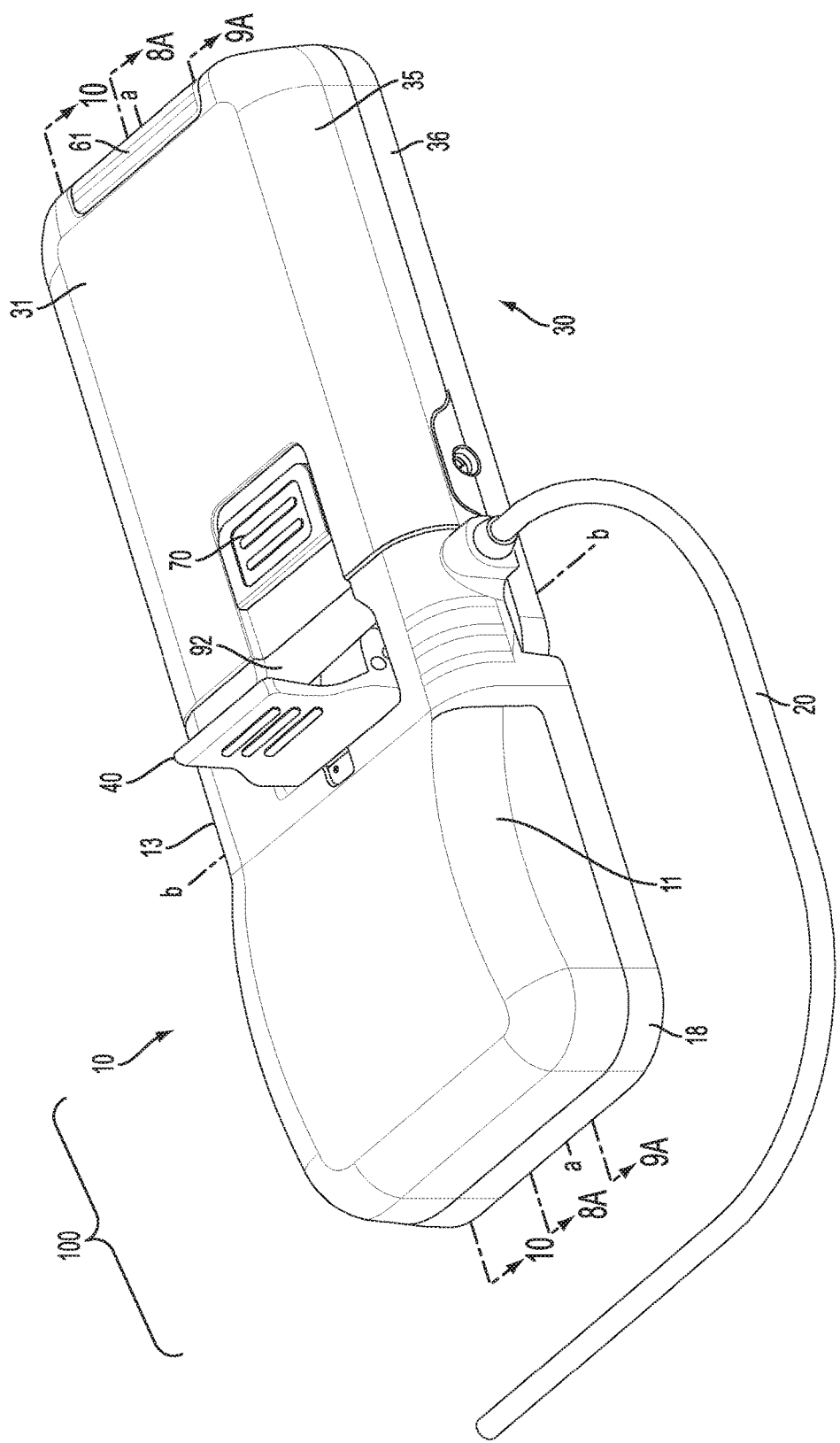
FIG. 2 is a perspective view of the device of FIG. 1, with the cassette received by the pump and the lock member in an open position.
Figure 3:
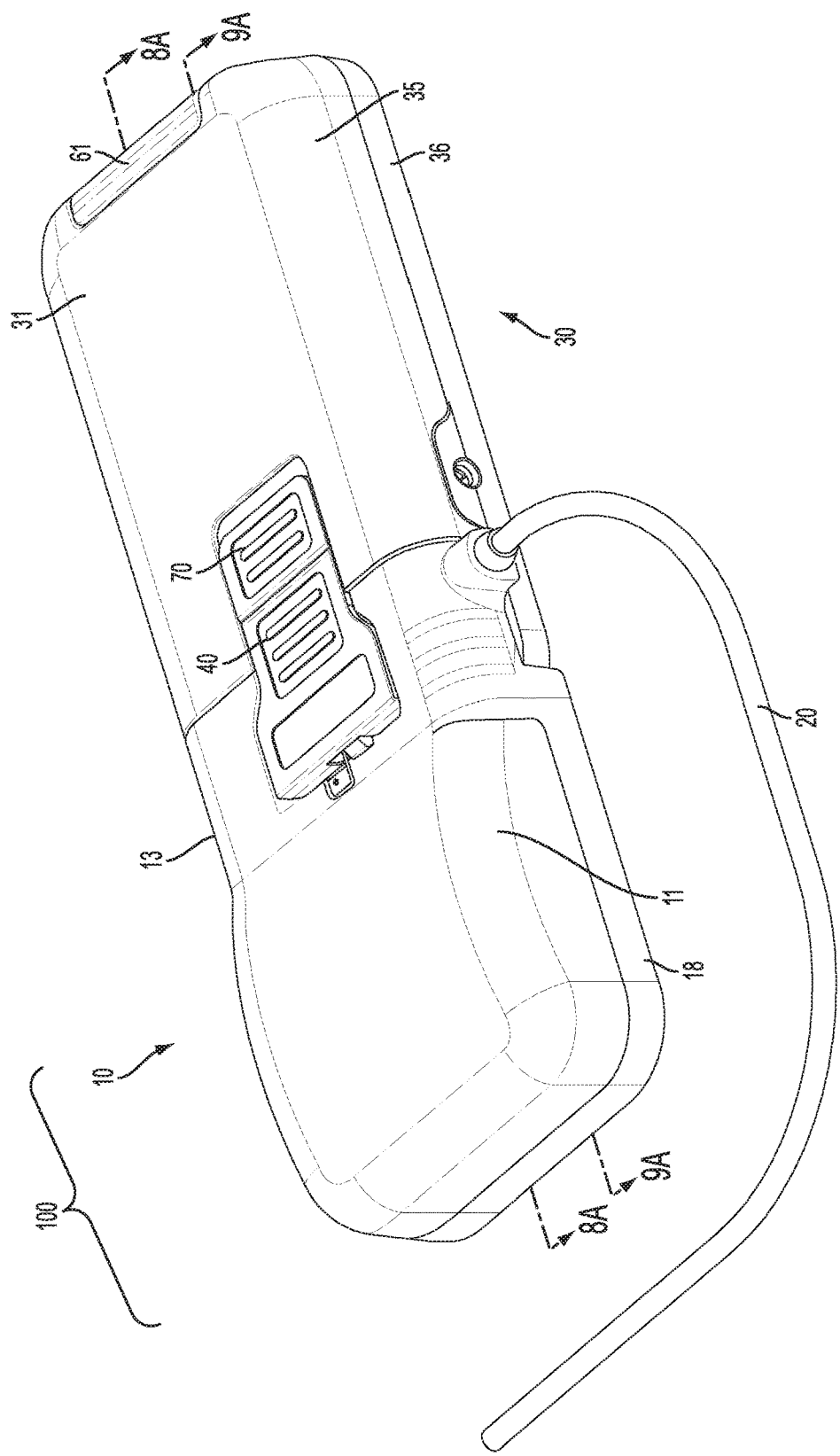
FIG. 3 is a perspective view of the device of FIG. 2, with the lock member in a closed position.
Figure 4A:
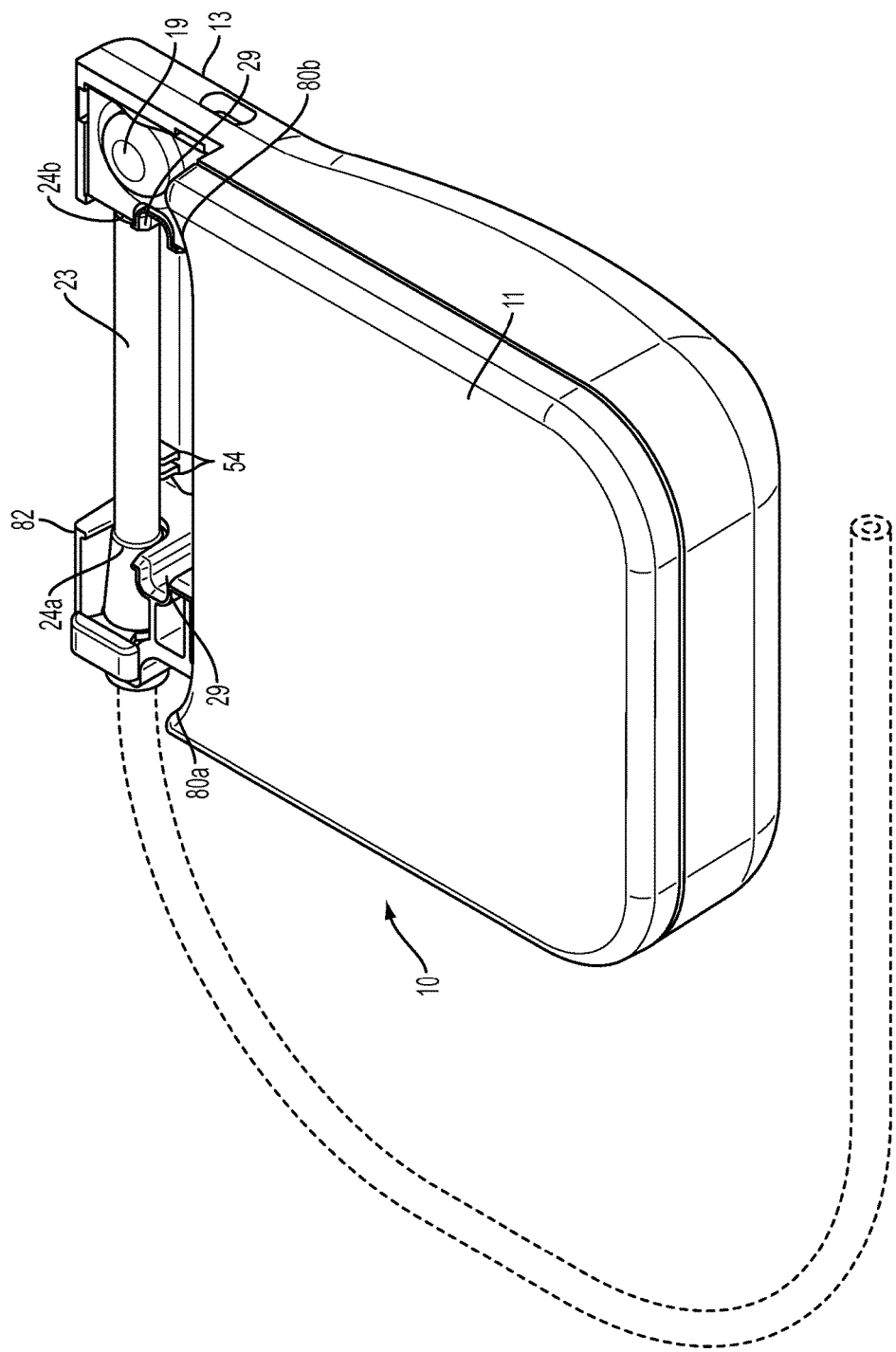
Figure 4D:
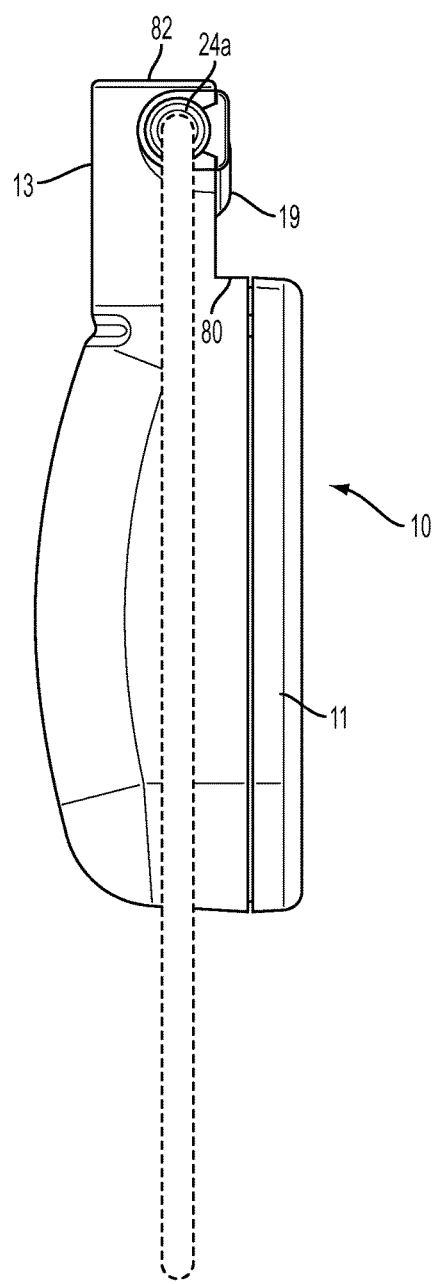
Figure 4E:
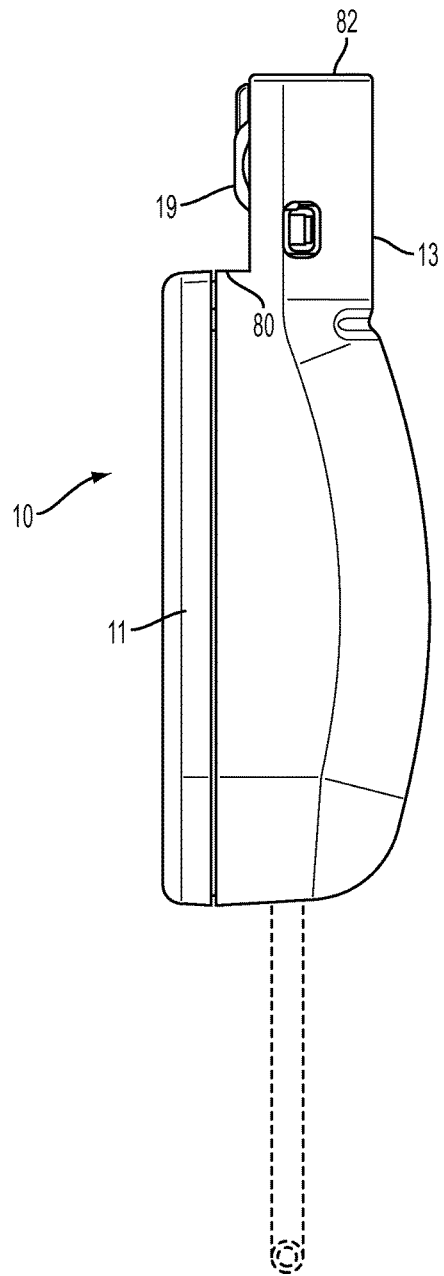

Referring to an illustrative embodiment of FIGS. 1-3, delivery device 100 includes a cassette 10 including a cassette housing 11. Cassette housing 11 can have a cassette body region 14. Cassette body region 14 can define an interior to contain a fluid reservoir 12 (shown for example in FIG. 13) within the cassette housing 11, as discussed further herein. Cassette body region 14 can be any suitable shape to accommodate a fluid reservoir 12. For example, and as embodied herein, cassette body region 14 can have a bulbous shape defining a curved surface proximate a back surface of the cassette housing 11, which can accommodate a fluid reservoir 12 having a similar size and shape. As embodied herein, cassette body region 14 can have a generally flat surface proximate front surface of cassette housing 11, opposite the back surface, which can allow cassette housing 11 to lay flat on a planar surface, such as a table, to facilitate a user to insert or remove cassette 10 from engagement with a pump 30, as discussed herein.

Furthermore, and as embodied herein, the cassette housing 11 can have a cassette base region 13 to join with the pump mechanism 30, as discussed further herein. As shown, for purpose of illustration and not limitation, cassette base region 13 can be disposed along a longitudinal axis, such as disposed along the longitudinal axis a from the cassette body region 14 defined along cassette 10.

The delivery device 100 also includes a pump 30, which can include a pump housing 31. With reference to FIGS. 1-3 and 5A-5G, the pump housing 31 can include a receiving region 32 to receive the cassette base region 13. For example, and as embodied herein, the receiving region can be disposed at one end of the pump 30. Referring now to FIGS. 1-3, the cassette base region 13 can be inserted into the receiving region 32 and secured to the pump 30 by closing lock member 40 into engagement with the cassette 10. As embodied herein, for illustration and not limitation, the lock member 40 is in the form of a lever, which closes over the cassette 10. In this manner, and as shown for example in FIGS. 9A-9D, the lock member 40 can also be configured to engage and secure peristaltic tube 23 to the pumping mechanism 30, as discussed further herein. The cassette 10 can be inserted into and removed from the receiving region 32 when the lock member 40 is in the open position. When the lock member 40 is in the closed position, the cassette 10 can be secured to the pump 30 with the cassette base region 13 disposed within the receiving region 32 and inhibited or prevented from disengagement from the pump 30.

Figure 5A:
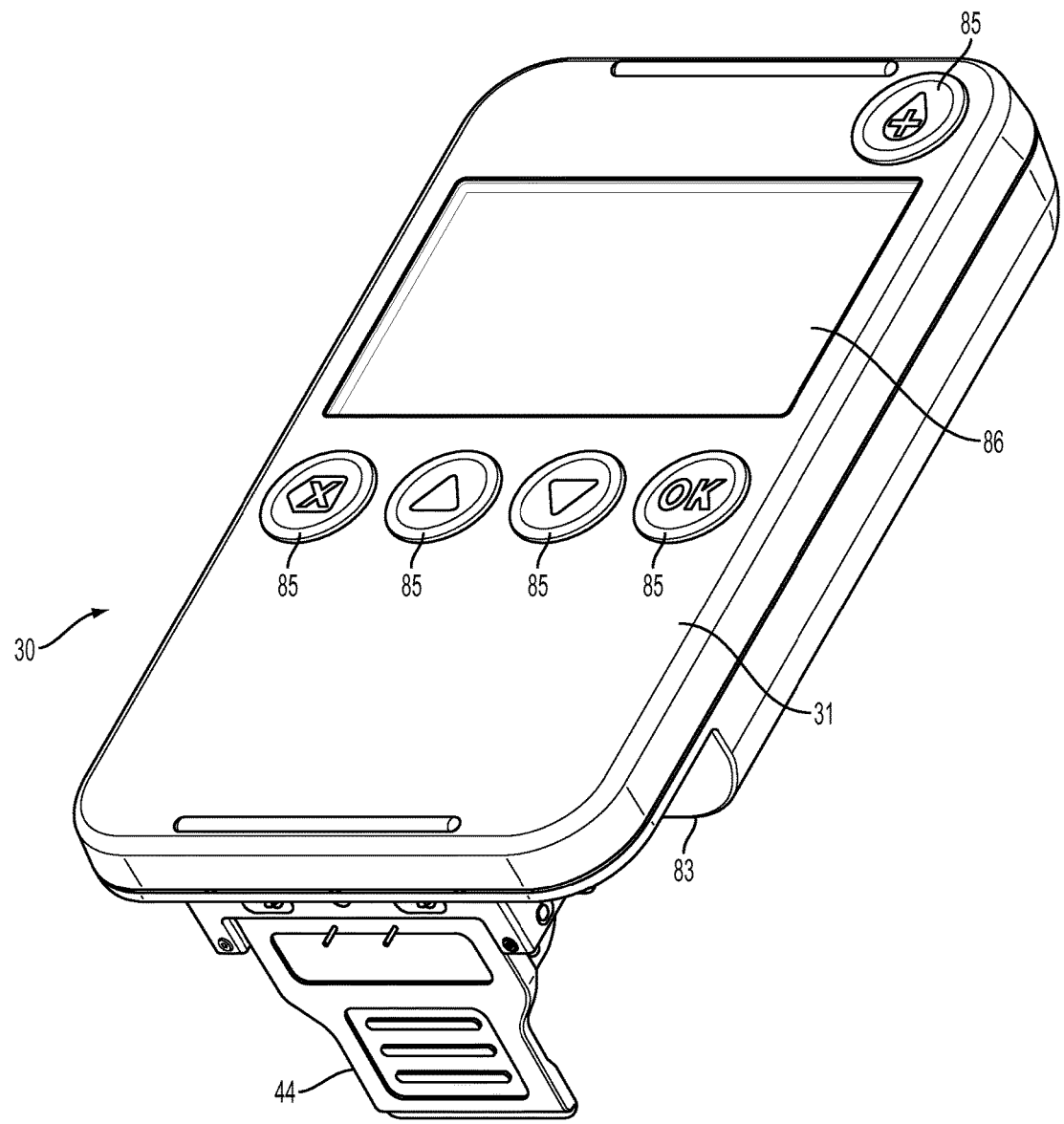
Figure 5B:
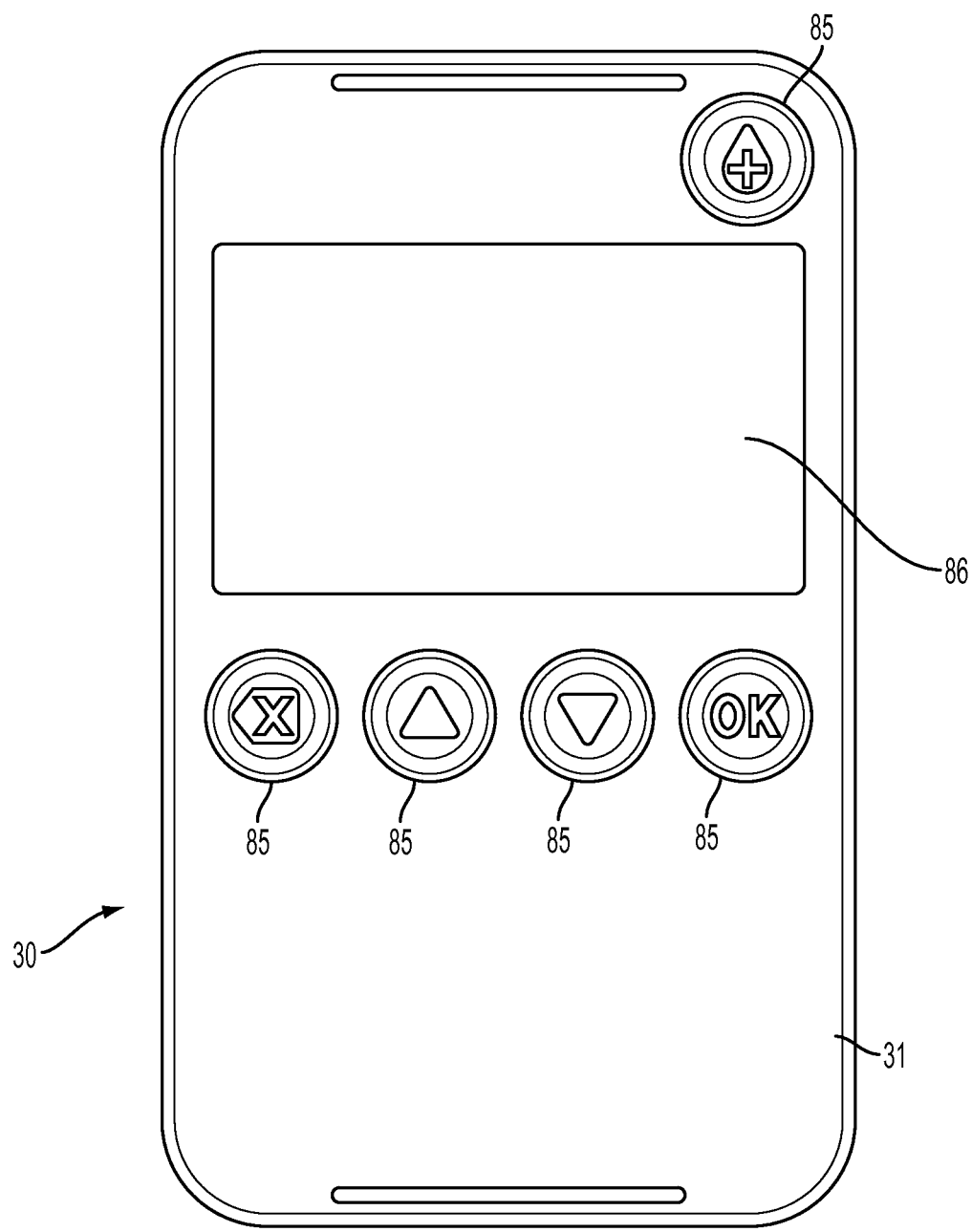

Additionally, with reference to FIGS. 5A-5B, pump housing 31 can include one or more inputs and outputs for interaction with a user. For example, and as embodied herein, pump housing 31 can include input buttons 85 disposed thereon, to provide, for example and without limitation, dosage settings and other device settings. Input buttons 85 can be formed using any suitable techniques. For example, and as embodied herein, input buttons 85 can be overmolded onto pump housing 31. Input buttons 85 can be formed of a material having a coefficient of static friction greater than that of the remainder of the pump housing 31, such as and without limitation, OM 3060-1 (GLS Corporation Versaflex®) and TM5ADT, TM6ADT and TM7ADT (each from Kraiburg TPE Corporation THERMOLAST®) which can, for example and without limitation, prevent sliding of pump housing 31 when disposed face down on a planar surface, such as a table, to facilitate a user to insert or remove cassette 10 from engagement with a pump 30, as discussed herein. Pump housing 31 can also include an output display 86. Output display 86 can be any suitable display to provide visual information to a user, for example and without limitation, an LCD or LED display or any other suitable display.

Referring now to FIGS. 4A-4G and 5A-5G, for the purpose of illustration and not limitation, the cassette 10 can be configured to be aligned and/or secured with the pump 30 via one or more features within the receiving region 32. For example, and as embodied herein, cassette base region 13 can define a boundary 28 to be received by receiving region 32 of the pump. As embodied herein, cassette base region 13 can include one or more rails 29 (as shown for example in FIG. 4B) configured to receive protrusions 33 of receiving region 32. As shown for example in FIG. 4B, cassette base region 13 can include a pair of opposing rails 29, which can be disposed on opposite sides of a longitudinal axis a defined by cassette 10, and can be substantially symmetrical about the longitudinal axis a. Additionally, and as embodied herein, each rail 29 can be recessed relative an adjacent portion of the boundary 28. As shown for purpose of illustration, rails 29 can be aligned along a transverse axis b defined across cassette 10. As embodied herein, each rail 29 can thus define an abutment surface generally parallel with the transverse axis b.

Figure 6:
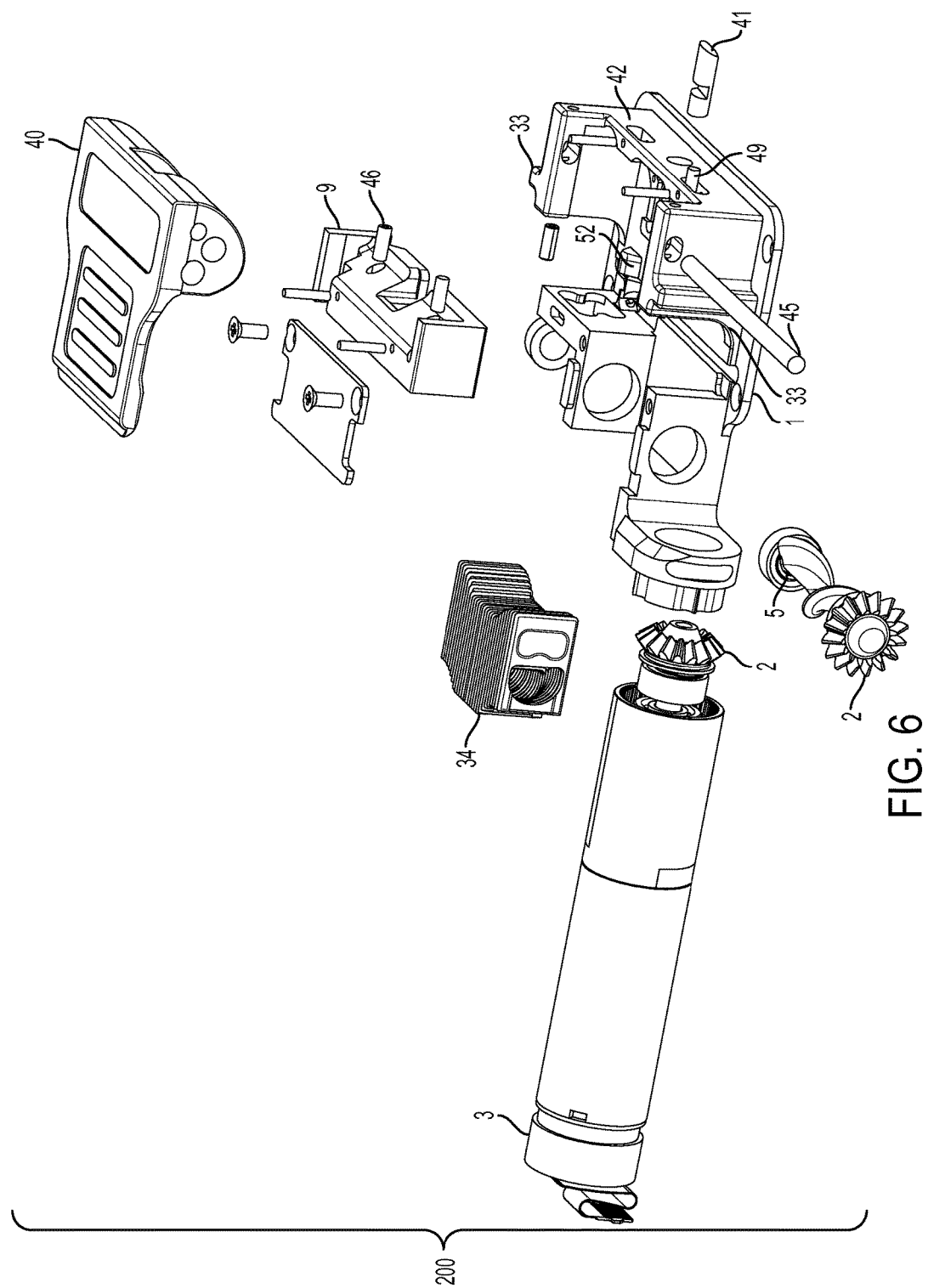
FIG. 6 is an exploded perspective view of an exemplary embodiment of a pump assembly in accordance with the disclosed subject matter.

Additionally, and as embodied herein, protrusions 33 to receive rails 29 can be formed in pump base block 1 (as shown for example in FIG. 6). For purpose of illustration, and as embodied herein, pump housing 31 can include one or more slots 39 (as shown for example in FIGS. 11A-11C) configured to receive protrusions 33 of the pump base block 1. Alternatively, the configuration of the rails and protrusions can be reversed, such that rails 29 are disposed on the cassette 10 and slots 39 are disposed on the pump 30.

Additionally or alternatively, and as embodied herein, the cassette 10 can be secured and aligned via an engagement surface 17, which can be received and captured by lock member 40 when in the closed position, as discussed further herein. Engagement surface 17 can be substantially coplanar with the back surface of the cassette housing 11. Alternatively, engagement surface 17 can include a recessed area 92 recessed relative the back surface of the cassette housing 11. For purpose of illustration, and as embodied herein, recessed area 92 can be shaped to receive and/or mate with at least a portion of lock member 40 when in the closed position, as shown for example in FIGS. 2-3. As such, and as embodied herein, recessed area 92 can taper to a smaller cross dimension toward an end 82 of the cassette housing 11, as shown for example in FIG. 4C. With reference to FIG. 4B, as embodied herein, the engagement surface 17 can be configured as an elongated strip of material to be engaged by lock member 40 when closed about engagement feature 17. In this manner, engagement surface 17 can form a unitary bridge across the longitudinal axis a. Alternatively, engagement surface 17 can include a pair of engagement surface portions on opposite sides of the longitudinal axis a, and in some embodiments, the pair of engagement surface portions can be substantially symmetrical about the longitudinal axis a.

Additionally or alternatively, and as embodied herein, the cassette 10 can be secured and aligned with the pump 30 via alignment pin 41 in the locking mechanism. As such, and as embodied herein, cassette base region 13 can include an alignment key 44 defining a receiving recess to receive alignment pin 41. For purpose of illustration and not limitation, and as embodied herein, alignment key 44 can be centered between the lateral side walls of cassette housing 11. As embodied herein, alignment key 44 can project into the boundary 28, and in some embodiments, alignment key 44 can project from the cassette body region 14 into the cassette base region 13. Alignment key 44 can have any suitable shape to receive alignment pin 41. For example and not limitation, alignment key 44 can be cylindrical, channel-shaped or any other suitable shape. Additionally or alternatively, as shown for example in FIG. 8B, the receiving recess formed by alignment key 44 can be tapered along the longitudinal axis a to assist with receipt and alignment of alignment pin 41 therein.

Figure 5C:
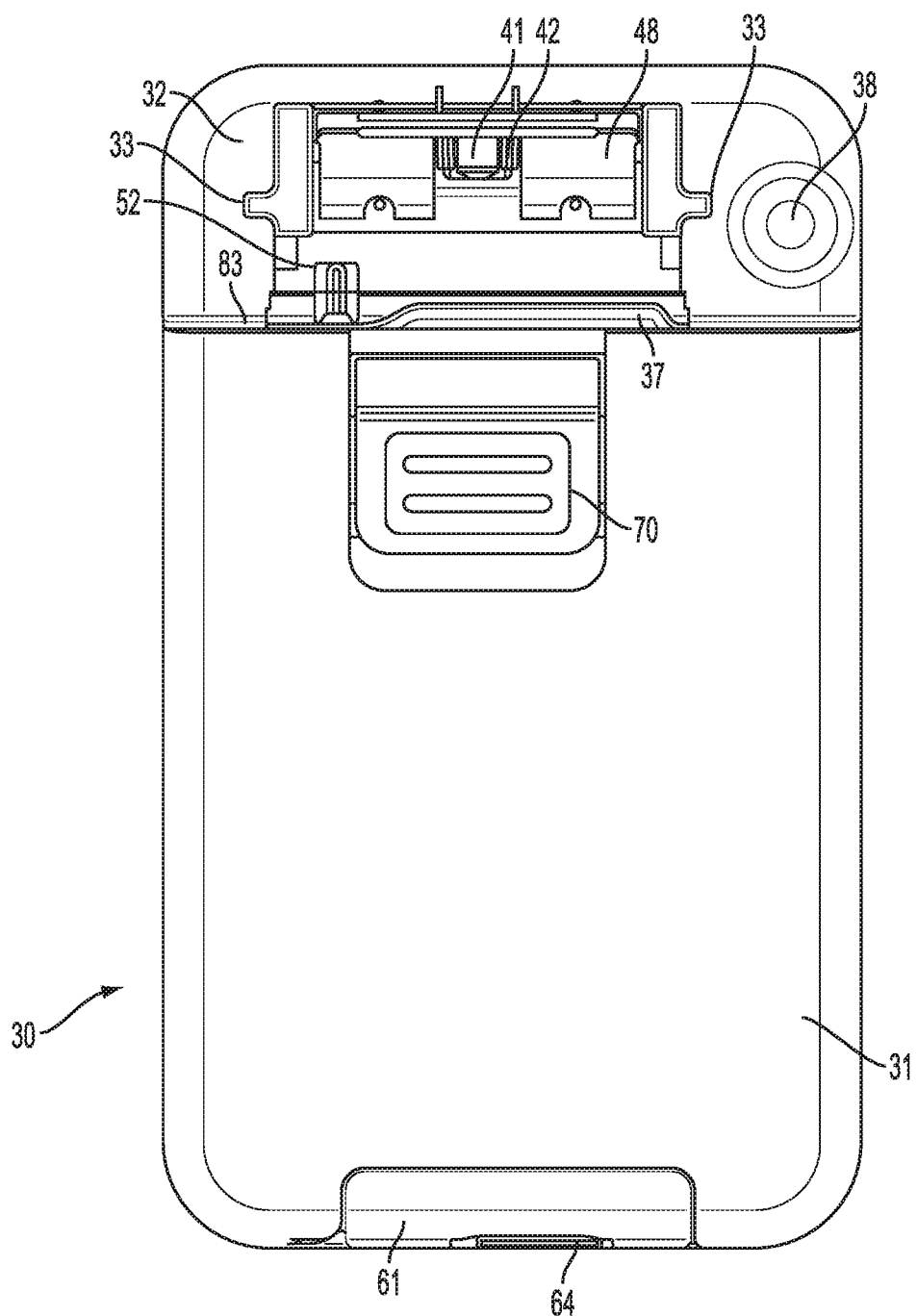
Figure 5F:
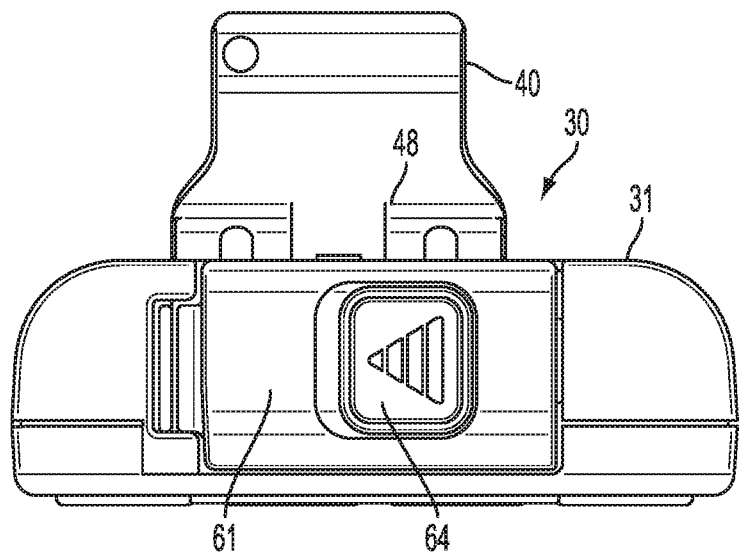
Figure 5G:
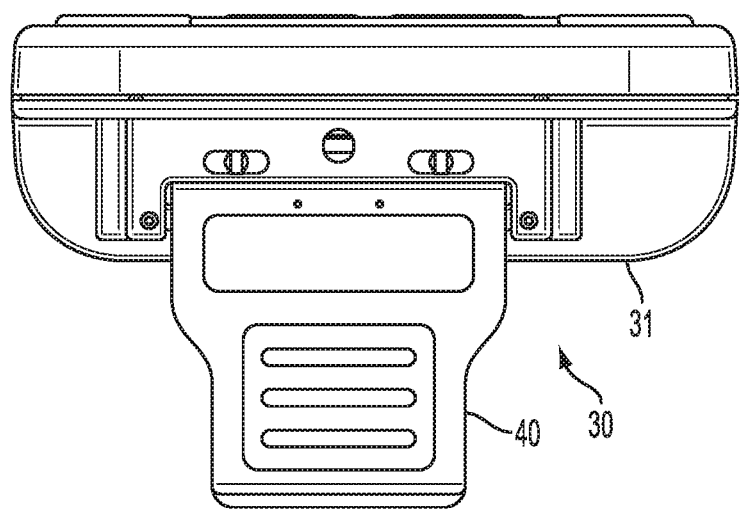
Figure 8B:
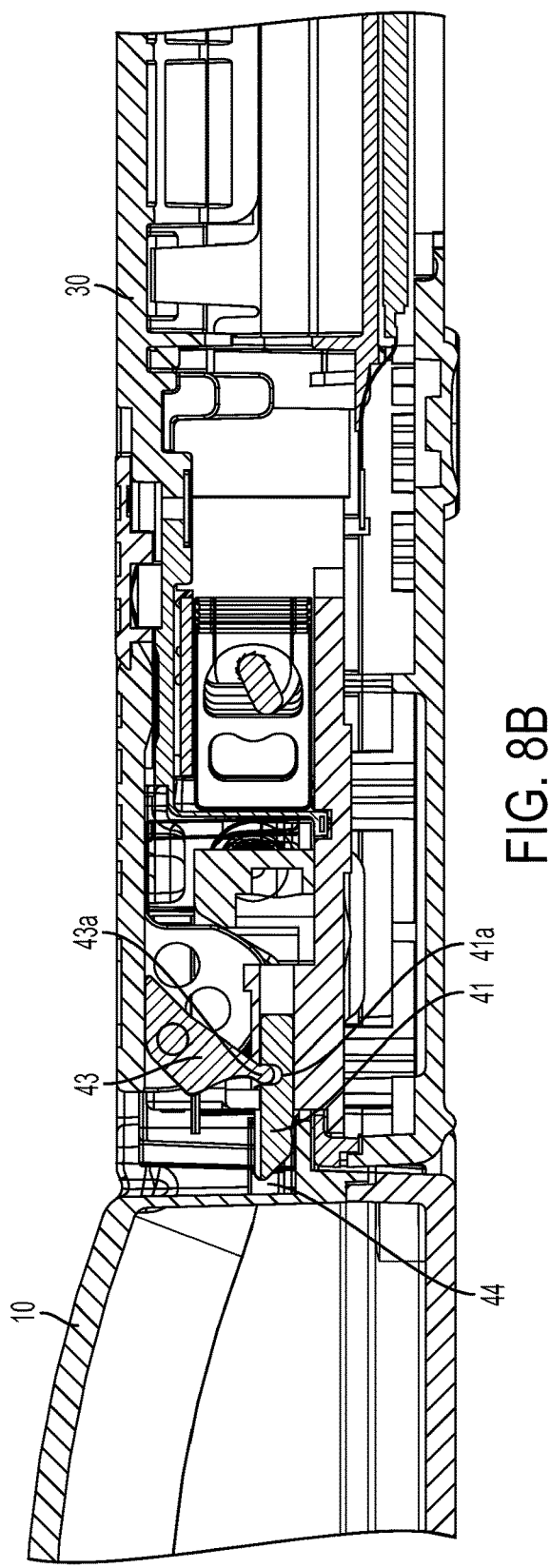
FIG. 8B is a cross-sectional view of the exemplary device taken along line 8B-8B of FIG. 3.

For purpose of illustration and not limitation, as shown for example in FIGS. 5C and 8A-8B, lock member 40 can be biased, such as by a torsion spring 42, to urge lock member 40 toward the open position. Additionally, and embodied herein, lock member 40 can include a pin driver 43, which can have a projection 43a received in notch 41a of alignment pin 41. As embodied herein, pin driver 43 can be urged upon movement of lock member 40 toward the open position to drive the alignment pin 41 away from alignment key 44 in the disposable cassette housing 11 (as shown for example in FIG. 8A). With reference to FIG. 8B, when the lock member 40 is moved to the closed position, the lock member 40 urges the pin driver 43 to drive the alignment pin 41 into the alignment key 44 of the cassette housing 11. For purpose of illustration and not limitation, as embodied herein, the alignment pin 41 can be tapered. The material for the alignment pin 41 can be stainless steel.

Additionally or alternatively, as further embodied herein, cassette 10 can include support rib 54 as shown in FIG. 4B. In this manner, and as embodied herein, pump 30 can include a tubing guide ridge 52 (as shown for example in FIG. 5C), which can engage or restrict movement of the peristaltic tube 23 when the cassette 10 is received within the receiving region 32. When the cassette 10 is received within the receiving region 32, tubing guide ridge 52 can align with support rib 54 (as shown for example in FIG. 4B) on the cassette base region 11, for example and as embodied herein to guide peristaltic tube 23 into engagement with an occlusion sensor. For purpose of illustration, and as embodied herein, support rib 54 can project from boundary 28. Additionally, and as embodied herein, support rib 54 can include a pair of support rib portions. Alternatively, support rib 54 can be configured as a single, unitary rib. As shown in FIG. 4B, for purpose of illustration and not limitation, cassette housing 11 can include a pair of end fittings 24a, 24b to support peristaltic tube 23, and if provided, support rib 54 can be substantially aligned with end fittings 24a, 24b.

Additionally or alternatively, and as further embodied herein, cassette base region 13 can include a contoured surface 80 configured to mate with a corresponding contoured end 81 of pump 30, as shown in FIG. 1. For purpose of illustration, and not limitation, contoured surface 80 can include contoured end portions 80a, 80b having a concave contour relative cassette base region 13 proximate opposing sides of cassette base region 13. Additionally or alternatively, cassette base region 13 can include a selected flat surface 82 proximate an end of cassette housing 11. As embodied herein, flat surface 82 can include flat surface portion 82a, 82b proximate lateral side walls of cassette housing 11. Flat surface 82 of cassette base region 13 can be sized and shaped to engage corresponding flat surface 83 of receiving region 32 of pump 30.

These various features of the cassette base region can be combined in various combinations and arrangements as desired. For example and not limitation, the cassette can be provided with the rails and engagement surface, without an alignment key if desired. Likewise, and without limitation, the cassette can be provided with a pair of alignment keys each offset from the longitudinal axis a.

According to another aspect of the disclosed subject matter, a device for delivering a beneficial agent is provided. The device generally includes a cassette, a pump, a delivery tube and a lock member. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component. The pump housing has a receiving region to receive the cassette base region. The fluid drive component is disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region and a length of the delivery tube in operative engagement with the fluid drive component when the lock member is in the closed position.

Additionally, and as embodied herein, an alignment pin can be operatively coupled to the lock member. Movement of the lock member between the open position and the closed position can extend at least a portion of the alignment pin into engagement with the cassette housing. The cassette housing can define a receiving recess proximate the cassette base region to receive the alignment pin when the lock member is moved toward the closed position. The receiving recess can be tapered toward a closed end. For example, the receiving recess can be defined by an alignment key, such as an alignment key, projecting from the cassette body region into the cassette base region. The alignment pin can include a tapered end. To move the alignment pin into an extended position, the lock member can include a protrusion, and the alignment pin can include a notch to receive the protrusion to engage the lock member to operatively couple the alignment pin to the lock member. Furthermore, and as embodied herein, the lock member can include a latch, and receiving region can further include a torsion spring mechanically coupled to the lock member to urge the latch toward the open position.

In addition, and as embodied herein, the latch can further include a latch cam surface, and the pump can further include an occlusion block disposed proximate the receiving region and having an occlusion block cam surface. The occlusion block can be biased to urge the occlusion block cam surface against the latch cam surface. The latch cam surface and the occlusion block cam surface thus can be configured to urge the occlusion block toward an operative position to hold the peristaltic tube in functional relationship to the fluid drive component when the latch is moved from the open position toward the closed position. The latch cam surface and the occlusion block cam surface can be configured to define a dead zone where the occlusion block remains in the operative position during continued movement of the latch continues from the open position to the closed position. The dead zone can be defined by 10 degrees of final movement of the latch from the open position to the closed position. The latch comprises a pivotal latch mounted on a hinge. Alternatively, the latch can include a draw latch mounted for sliding movement. The features of this aspect can be combined with one or more feature of the apparatus and methods set forth above.

With reference to FIG. 6, the pump housing 31 can include a pump assembly 200 having a fluid drive component. The pump assembly 200 can be configured, for example, as a peristaltic pump. For example, a peristaltic pump can include a motor 3, a cam shaft 2, and a plurality of finger plates 34 disposed along the length of the camshaft 2. The camshaft 2 is coupled to the motor 3 for rotation about a longitudinal axis a of the cam shaft 2, and has at least one radially-outward projection 5 defining a helical engagement portion disposed along a length of the camshaft 2. The plurality of finger plates 34 are disposed along the length of the cam shaft 2. Each finger plate 34 is mounted for movement in a transverse direction relative to the longitudinal axis a of the camshaft 2, and has an aperture defined therein to receive the cam shaft 2 therethrough. Additional details of suitable fluid drive components and related features of the pump suitable for use herewith are described in concurrently filed applications by Applicant, each entitled "PUMP, MOTOR AND ASSEMBLY FOR BENEFICIAL AGENT DELIVERY" Ser. Nos. 14/586,923; 14/586,927; and 14/586,930, each of which is incorporated by reference in its entirety.

Figure 7A:
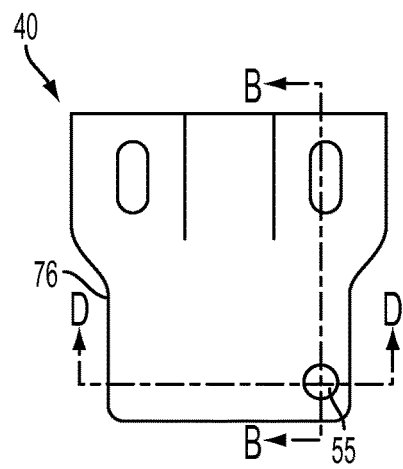
FIG. 7A a bottom view of an exemplary lock member of the pump of FIG. 1.
Figure 7B:
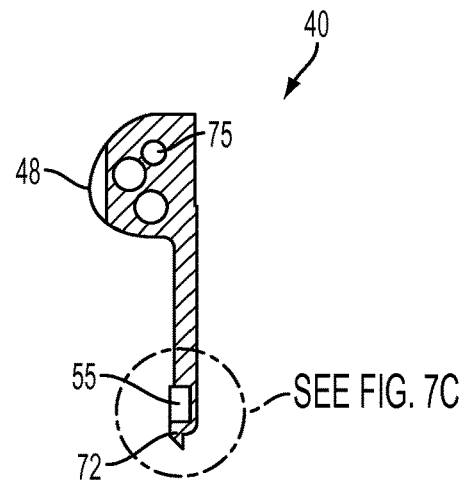
FIG. 7B is a cross-sectional view of the exemplary lock member taken along line B-B of FIG. 7A.
Figure 7C:
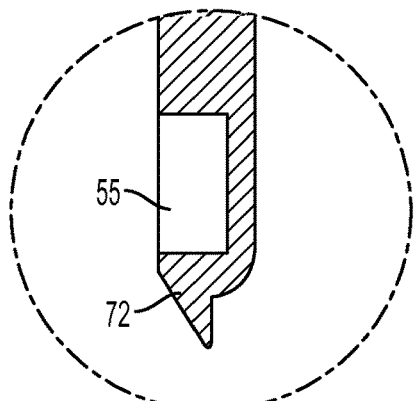
FIG. 7C is a detailed view of region 7C of the cross section of the exemplary lock member of FIG. 7B.
Figure 7D:
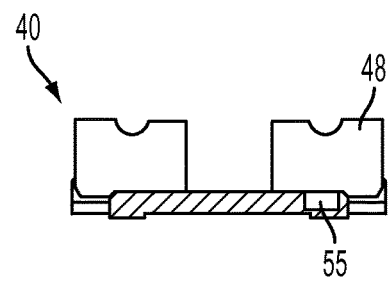
FIG. 7D is a cross-sectional view of the exemplary lock member taken along line D-D of FIG. 7A.
Figure 7E:
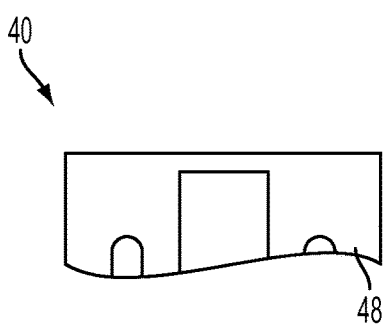
FIG. 7E is a partial rear view of the exemplary lock member of FIG. 7A.
Figure 7F:
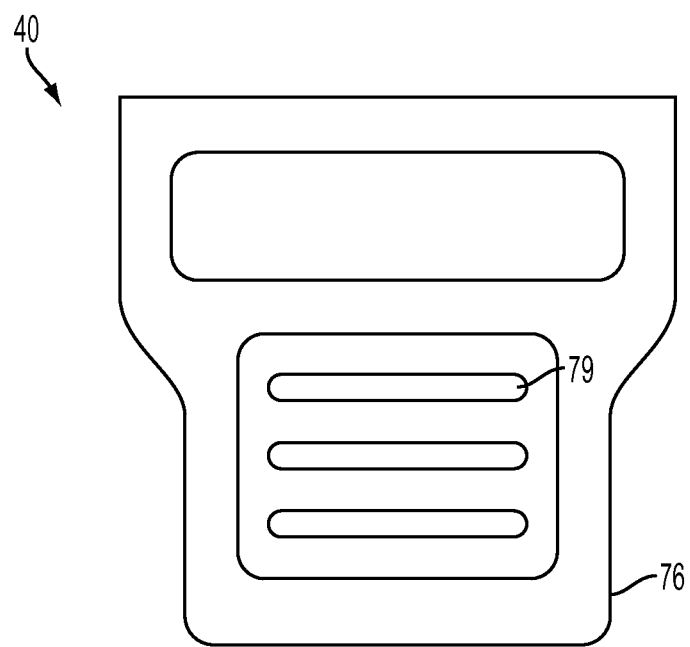
FIG. 7F is a top view of the exemplary lock member of FIG. 7A.
Figure 7G:
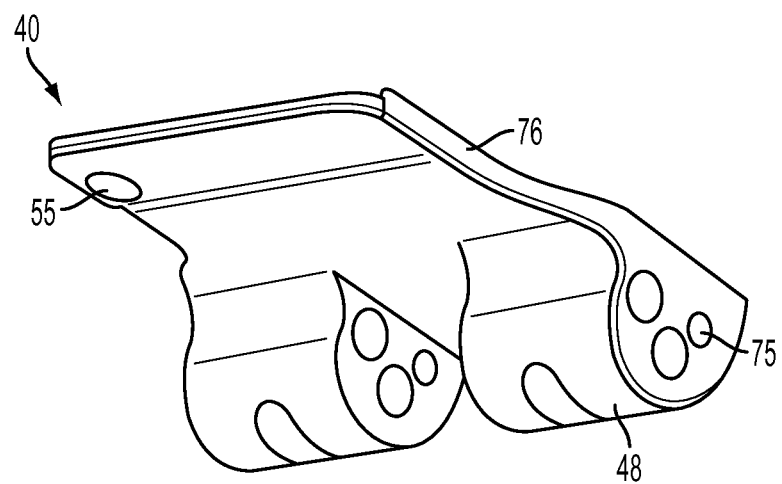
FIG. 7G is a bottom perspective view of the exemplary lock member of FIG. 7A.

For purpose of illustration and not limitation, as embodied herein, lock member 40 can be configured as a latch or cam lever, such as a pivotal latch, a draw latch, or any other suitable latching mechanism. As shown for example in FIGS. 6 and 7A-7G, lock member 40 can be configured as a pivotal latch. Lock member 40 can include a latch cam surface 48 to engage an occlusion block, as discussed further herein. Additionally, and as embodied herein, lock member 40 can include a hinge receptacle 75 to receive a hinge pin 45 to allow pivotal movement of lock member 40. As embodied herein, hinge pin 45 can also engage pin driver 43 to lock member 40 to allow pivotal movement of pin driver 43 with lock member 40, as discussed further herein. Additionally, lock member 40 can be biased toward an open position, such as by torsion spring 42. Furthermore, and as embodied herein, lock member 40 can include a closure sensor receptacle 55 to receive a closure sensor, such as for purpose of illustration and not limitation, as embodied herein, a magnet to trigger a reed sensor, as discussed further herein. As shown in FIG. 7A, and as embodied herein, lock member 40 includes a tapered end 76 sized and shaped to engage a corresponding recess in cassette base region 13, as discussed further herein. As shown in FIG. 7F, for purpose of illustration and not limitation, lock member 40 can include one or more raised surface features 79 to assist with engagement of lock member 40, for example by a user, to move lock member 40 between the open position and closed position.

Referring now to FIGS. 9A-9D, when the lock member 40 is moved into the closed position, the lock member 40, urged by torsion spring 42, pivots about the lever hinge 45. Tension springs 46 urge the occlusion block cam surface 47 of occlusion block 9 against the latch cam surface 48 of lock member 40. As such, and with reference to FIGS. 9A-9D, the occlusion block 9 can be positioned, by the stroke of the lock member 40, an appropriate distance to dispose the peristaltic tube 23 operatively against the peristaltic fingers 34 when closed, as shown for example in FIG. 9D.

As illustrated for example in FIG. 9C, with the lock member 40 within a certain angle of rotation α, for example and without limitation, within a range of approximately 0°-10° relative to the pump 30, the lock member lever cam surface 48 as embodied herein enters a so-called "dead zone." That is, within the "dead zone," the lock member 40 can continue to be closed and latch against the pump housing 31, while the occlusion block 9 remains positioned in a fully latched state. In this manner, the occlusion block 9 is properly positioned relative to the peristaltic fingers 34 even if the lock member 40 is not fully closed, and thus the effect of mechanical tolerances in the locking assembly on the position of the occlusion block 9 can be reduced. A closure indicator, embodied herein as a magnet disposed in closure sensor receptacle 55 of lock member 40, or other suitable closure elements, can be detected by a closure sensor, embodied herein as a magnetic field detector disposed in the pump housing 31 proximate the lock member 40 to allow the pump assembly to detect when the lock member 40 is fully closed.

Figure 9B:
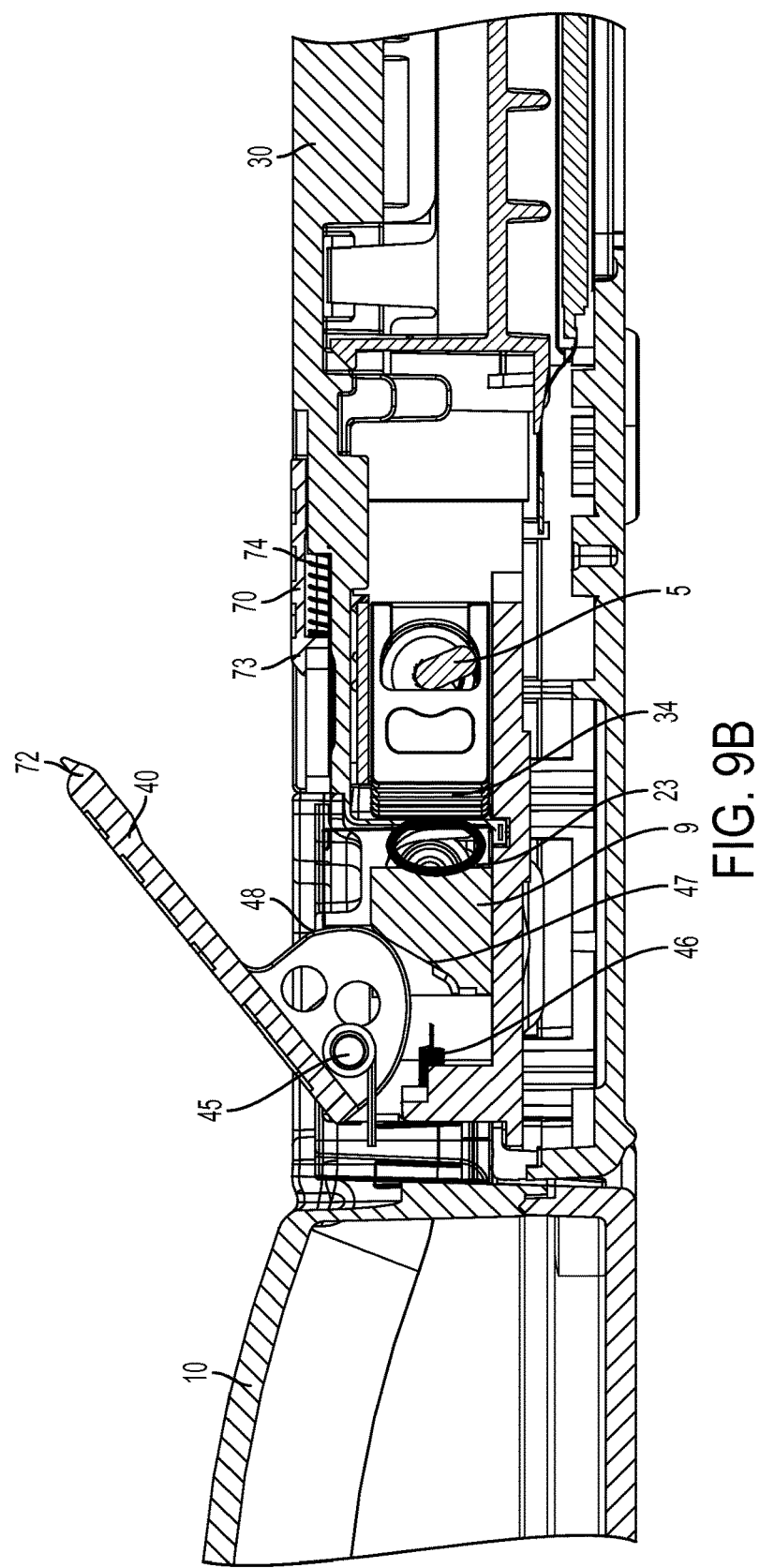
FIG. 9B is a cross-sectional view of the exemplary device of FIG. 9A, with the lock member urged from the open position toward the closed position.
Figure 9D:
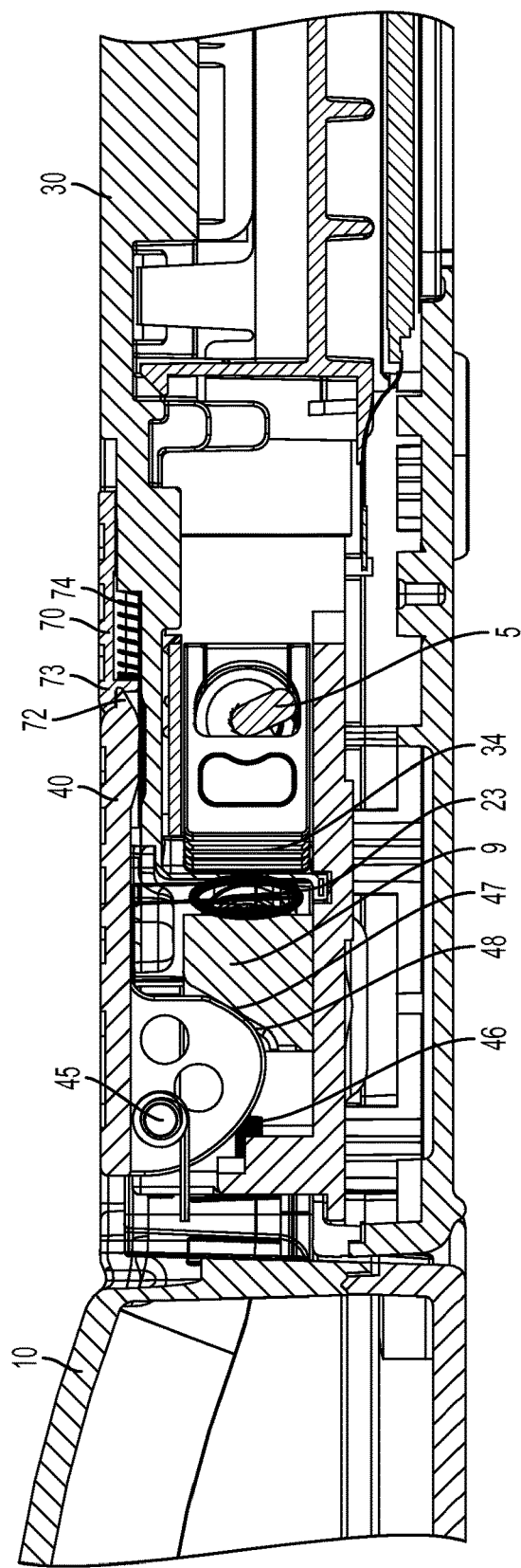
FIG. 9D is a cross-sectional view of the exemplary device taken along line 9D-9D of FIG. 3, with the lock member fully engaged.

As illustrated for example in FIG. 9D, with lock member 40 further urged into the closed position, distal projection 72 of lock member 40 moves along cam surface of lock member release 70 to urge lock member release 70 away from lock member 40 and allow distal projection 72 to move beyond and engage corresponding projection 73 of release 70. In this manner, lock member 40 is secured in the closed position by projection 73 of release 70, which is biased into engagement with lock member 40 by spring 74. To release lock member 40, lock member release 70 can be urged away from lock member 40 to move projection 73 out of alignment with distal projection 72 to allow lock member 40, which as described herein can be biased in the open position, to be urged into the open position, as embodied herein by torsion spring 42.

As illustrated for example in FIG. 6, in some embodiments, set screws 49 can be provided to the lever hinge pin 45 to allow for adjustment during assembly to account for mechanical tolerances and provide a suitable occlusion distance. Polishing the surface of lock member 40 can reduce friction between the occlusion block surface 47 and the lock member 40. The roughness average of the cam lever can be about 0.4 μm. This can be accomplished by one or more of tumbling, anodizing, and polishing the lock member 40. Additionally, providing an occlusion block cam surface 47 with a slope of 30 degrees can increase the vertical component of the force of the lock member 40.

According to another aspect of the disclosed subject matter, and further to the above a device for delivering a beneficial agent is provided. The device generally includes a cassette, a pump, a delivery tube and a lock member. The cassette includes a cassette housing with a fluid reservoir defined therein. The cassette housing has a cassette base region, and the cassette base region includes a radio frequency identification (RFID) shell housing a RFID tag. The delivery tube is fluidly coupled with the fluid reservoir. The pump includes a pump housing containing a RFID reader and a pump assembly having a fluid drive component. The pump housing has a receiving region to receive the cassette base region. The RFID reader and the fluid drive component are disposed proximate the receiving region. The lock member is coupled to the pump housing and is movable between an open position and a closed position. The cassette is capable of being inserted into and removed from the receiving region when the lock member is in the open position. The cassette is secured to the pump with the cassette base region within the receiving region with the RFID tag disposed proximate the RFID reader and a length of the delivery tube in operative engagement with the fluid drive component when the lock member is in the closed position.

Additionally, and as embodied herein, the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent.

Furthermore, and as embodied herein, the receiving region can further include a RFID receiving region with the RFID reader housed therein. The RFID receiving region can be configured to engage the RFID shell when the cassette is secured to the pump with the cassette base region within the receiving region of the pump housing. The RFID receiving region can have a shape configured to mate with the RFID shell. For example, the RFID shell can include a raised surface relative an adjacent surface of the cassette base region, and the RFID receiving region can include a dimple configured to receive the raised surface when the cassette is secured to the pump with the cassette base region within the receiving region of the pump housing. The RFID shell and RFID receiving region can be configured to dispose the RFID tag within about 5 mm of the RFID reader when the cassette is secured to the pump with the cassette base region within the receiving region of the pump housing. The RFID reader can have a range of detection configured to read the RFID tag only when the RFID receiving region is in engagement with the RFID shell. The device can further include a processor coupled to the RFID reader and configured to verify identification information for the cassette encoded on the RFID tag. Additionally or alternatively, the processor can be coupled to the RFID reader and configured to enable operation of the pump if an expiration date of the beneficial agent encoded on the RFID tag is not exceeded. In addition or as a further alternative, the processor can be coupled to the RFID reader and configured to determine one or more dosing options based at least in part on a concentration of the beneficial agent encoded on the RFID tag. The RFID tag can include high or ultra-high radio frequency ID.

According to another aspect of the disclosed subject matter, and further to the above, a drug delivery reservoir cassette for a pump having an RFID reader, a receiving region configured to receive the cassette, and a lock member movable between an open position and a closed position is provided. The cassette includes a cassette housing with a fluid reservoir defined therein. The cassette housing has a cassette base region. The cassette base region includes a radio frequency identification (RFID) shell housing a RFID tag configured to be read by the RFID reader. The cassette is capable of being inserted into and removed from the receiving region when the lock member is in the open position, and the cassette is secured to the pump with the cassette base region within the receiving region with the RFID tag disposed proximate the RFID reader when the lock member is in the closed position.

The cassette can include any combination of features described herein. For example, and as embodied herein, the RFID shell comprises a raised surface relative an adjacent surface of the cassette base region. the RFID shell can include a raised surface relative an adjacent surface of the cassette base region. The raised surface can have a height of about 2 mm relative the adjacent surface. The receiving region can include a dimple having a bottom radius of 2.5 mm and a top radius of 6.25 mm, each as measured from an exterior of the pump housing. The RFID tag can be molded in the RFID shell. Additionally or alternatively, the RFID tag can be bonded to the RFID shell. The RFID tag can include identification information for the cassette encoded thereon. The RFID tag can include attribute information of a beneficial agent contained in the fluid reservoir encoded thereon. The attribute information can include one or more of a concentration, a formation date, and an expiration date of the beneficial agent. The features of these aspects can be combined with one or more features of the apparatus and methods set forth above.

Figure 10:
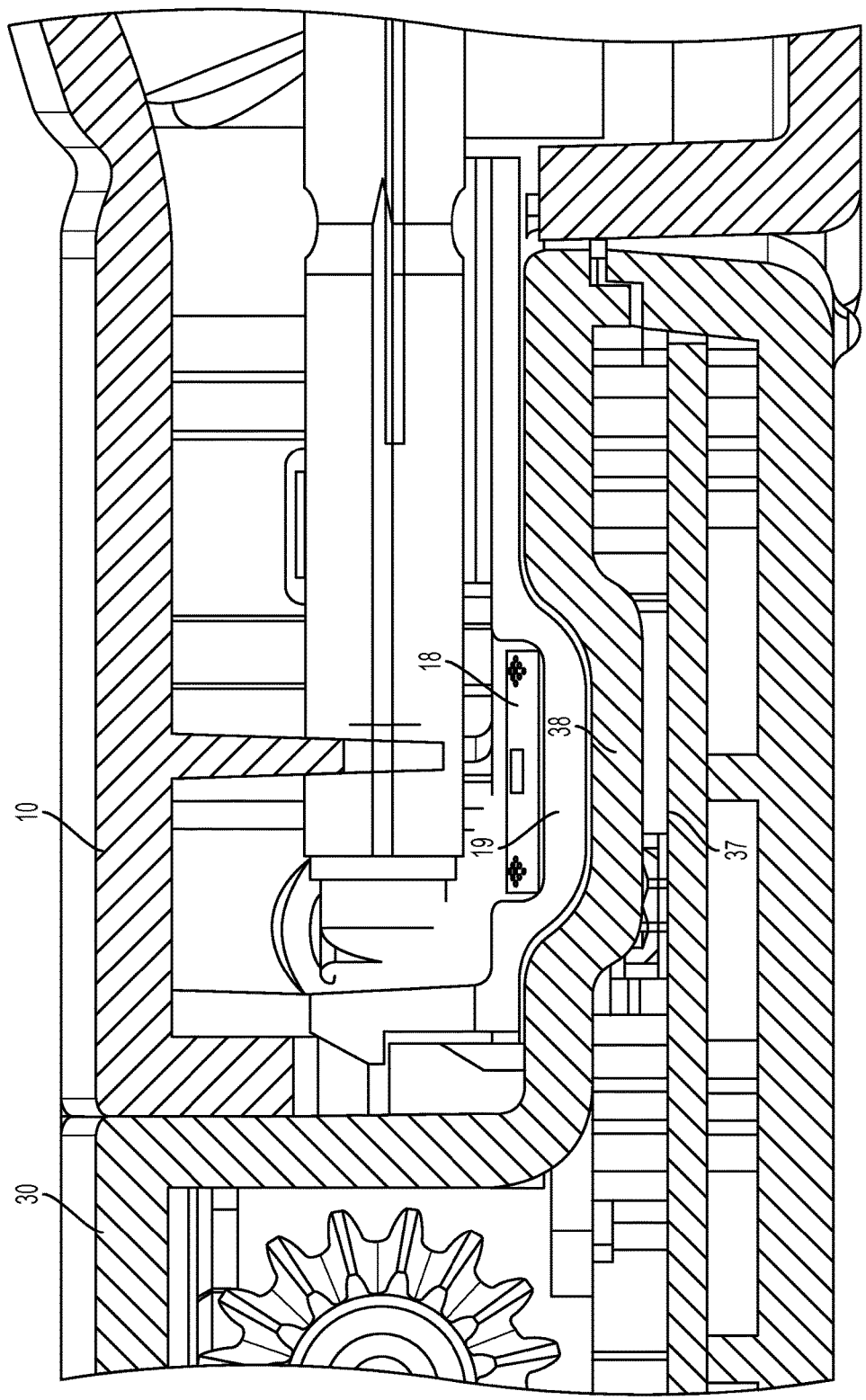
FIG. 10 is a cross-sectional view of the exemplary device taken along line 10-10 of FIG. 3.

For example and as embodied herein, cassette 10 can include an RFID enclosure shell to house an RFID tag. RFID enclosure shell can be configured to engage RFID tag with a corresponding RFID reader in pump 30. With reference to FIGS. 4B and 10, for purpose of illustration and not limitation, the RFID enclosure shell 19 can be shaped as a raised surface projecting into cassette base region 13. As shown for example in FIG. 10, RFID tag 18 be disposed within RFID enclosure shell 19 by any suitable technique. For example and without limitation, RFID tag 18 can be injection molded into the RFID enclosure shell 19. Alternatively, the RFID tag 18 can bonded to the RFID enclosure shell 19, for example by a potting technique, such as epoxy potting.

Referring now to FIGS. 5C and 10, as embodied herein, the pump housing 31 can have a RFID receiving region 38 to house an RFID reader 37 and can engage with the RFID enclosure shell 19 of the cassette housing 11. The RFID receiving region 38 can be configured as a dimple disposed in the receiving region 32 of the pump housing 31. For example, and as embodied herein, the dimple can be 1.9 mm deep, and can include a 2.5 mm bottom radius and a 6.25 mm top radius measured from the exterior of the pump housing 31. The RFID enclosure shell 19 and the RFID receiving region 38 can be configured to allow the RFID tag 18 to be disposed within 5 mm of an RFID reader 37 when the cassette housing 11 and the pump housing 31 are joined together, as described in further detail below. For purpose of illustration, and not limitation, as embodied herein, RFID reader 37 can be embedded in a circuit board disposed in pump housing 31. RFID reader 37 can be "box-shaped," such as a square or rectangular spiral, and formed by a number of wire windings, embodied herein as 14 coil windings, with 7 windings in each of two layers of the PCB. As such, RFID reader 37 can have outer cross-dimensions of 0.360"×0.372" and can have a central aperture having inner cross-dimensions of 0.204"×0.228". In this manner, RFID reader 37 can be configured with a range of detection to only detect RFID tag 18 when the cassette housing 11 is joined to the pump housing 31, such that another RFID tag further away from the RFID reader 37 would be outside the range of detection. Additionally or alternatively, the RFID reader 37 can be configured to determine which one of a plurality of RFID tags is closer to the RFID reader 37, and thus can determine which one of a plurality of cassette housings is joined to the pump housing 31. RFID reader 37 can utilize any suitable RFID techniques, including and without limitation, low, high, or ultra-high radio frequency ID.

RFID reader 37 also can be configured to identify drug cassettes and read information encoded in RFID tag 18. In this manner, the system can be used to detect cassettes that are not compatible or warrantied for use with the pump or otherwise to deter counterfeiting of drug cassettes. For purpose of illustration and not limitation, RFID tag 18 can include identification information for cassette 10 encoded thereon. Additionally or alternatively, RFID tag 18 can include attribute information of a beneficial agent contained in the fluid reservoir encoded thereon, which can include, without limitation, a concentration, a formation date, and/or an expiration date of the beneficial agent. RFID reader 37 can be coupled to a processor, which can be configured to receive and verify the identification information for cassette 10 encoded on the RFID tag, and can be further configured to enable operation of pump 30 only if the identification information for cassette 10 can be verified. Additionally or alternatively, the processor can be configured to enable operation of pump 30 only if an expiration date of the beneficial agent, if encoded on the RFID tag 18, is not exceeded. Additionally or as a further alternative, processor coupled to RFID reader 37 can be configured to determine one or more dosing options based at least in part on a concentration of the beneficial agent contained within cassette 10, if encoded on the RFID tag 18.

The housing provided herein can be made of a variety of constructions and configurations. For example, and not limitation, with reference to FIGS. 1-3 and 5C, the pump housing 31 can include a rear closure portion 35 and a front closure portion 36. One of the closure portions, such as the rear closure portion 35 as embodied herein, can include a membrane 37 disposed between the receiving region 32 and the fluid drive component, as embodied herein, to cover the finger plates of the peristaltic pump. In such a configuration, the finger plates of the peristaltic pump will push on the peristaltic tube 23 with the membrane 37 disposed in-between the fingers and the peristaltic tube 23. The membrane 37 can prevent debris and fluid from contacting and interfering with the pumping mechanism. The membrane 37 can be a thermoformed or injection molded membrane, which can be over-molded onto the rear closure portion 35. As embodied herein, the membrane 37 can define a rectangular-shaped protrusion extending from an end of the rear closure portion 35. Membrane 37 can define vertical sides extending from the rear closure portion 35 and forming slightly rounded corners at an outer face of the membrane 37. Additionally or alternatively, membrane 37 can have a first side extending from the rear closure portion 35 to the outer face of the membrane 37 at a gradual slope, and can have an opposing side extending vertically from the rear closure portion 35 and forming rounded corners proximate the outer face of the membrane 37. In this manner, the gradual slope formed proximate the inlet side of the peristaltic tube 23 can allow for a more gradual compression of the peristaltic tube 23.

Furthermore, and as embodied herein, the membrane 37 can be formed having dimensions and using materials to reduce rigidity, and thus utilize less force from the pump to move the membrane 37 and engage the peristaltic tube 23. For example, increased thickness of the membrane 37 can cause increased force applied by the pump during operation, and thus, increased power utilized and decreased battery performance. As such, the membrane 37 can have a thickness between 0.009 inches and 0.019 inches, and in some embodiments can have a thickness between 0.009 inches and 0.015 inches, which can provide suitable protection from debris and fluid ingress with suitable battery consumption. The material properties of the membrane 37, including flexibility, can similarly affect battery performance. In some embodiments, the membrane can be formed from Elastollan C80A, Estane 2103-90A, Elastollan S85A, Elastollan S95A or other suitable materials.

Figure 11A:
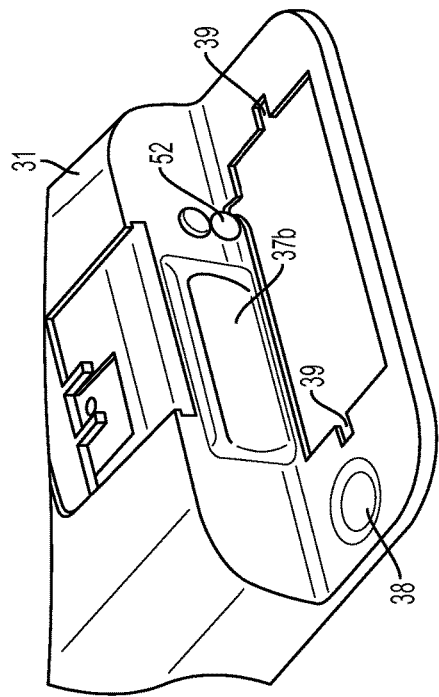
FIG. 11A is an enlarged perspective view of an alternative embodiment of a membrane for a pump housing in accordance with the disclosed subject matter.
Figure 11B:
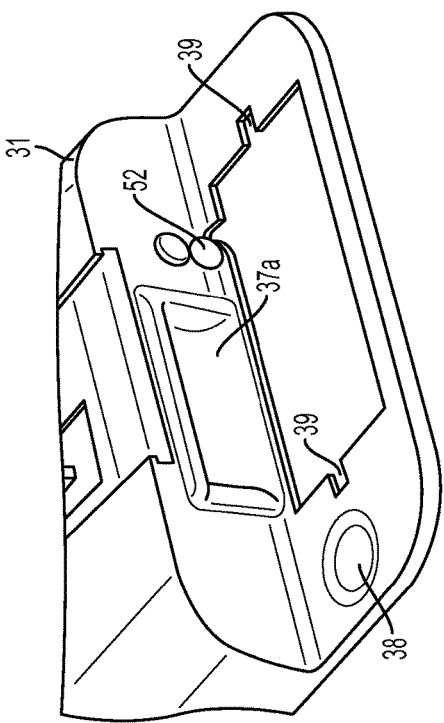
FIG. 11B is an enlarged perspective view of another alternative embodiment of a membrane for a pump housing in accordance with the disclosed subject matter.
Figure 11C:
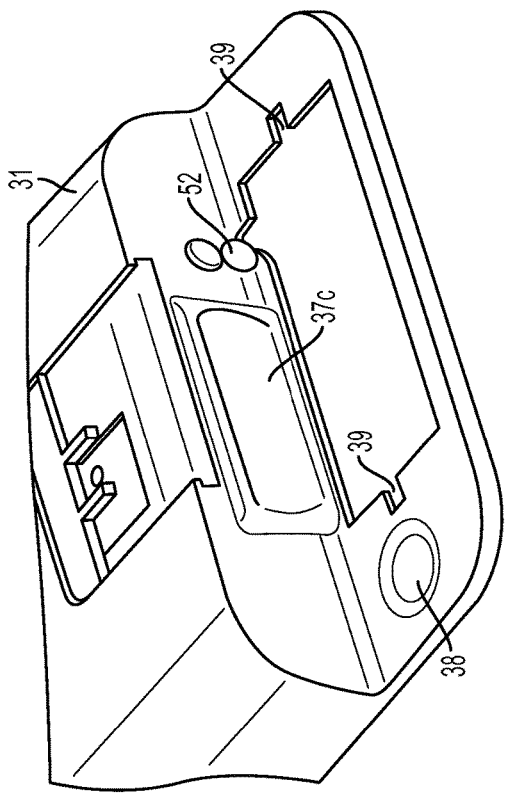
FIG. 11C is an enlarged perspective view of yet another alternative embodiment of a membrane for a pump housing in accordance with the disclosed subject matter.

Referring now to FIGS. 11A-11C, alternative embodiments of a membrane 37 are illustrated. As shown for example in FIG. 11A, membrane 37a can include rounded corners on each end of membrane 37a, and each rounded corner can be tapered inward toward a center of membrane 37a. Alternatively, as shown for example in FIG. 11B, membrane 37b can include rounded corners on each end of membrane 37b, and each rounded corner can be tapered outward away from a center of membrane 37b. As a further alternative, as shown for example in FIG. 11C, membrane 37c can include rounded corners on each end of membrane 37c, one of the rounded corners being tapered inward toward a center of membrane 37c and one of the rounded corners being tapered outward away from a center of membrane 37c. In each configuration, the curvature formed proximate the inlet side and outlet side of the peristaltic tube 23 can allow for peristaltic tube 23 to expand more easily after compression. For example and without limitation, as embodied herein, the curvature proximate the inlet side can reduce or prevent contact with one or more end fittings or joints proximate inlet side of peristaltic tube 23. Additionally or alternatively, the curvature formed proximate the outlet side can prevent or inhibit the membrane from being urged away from the occlusion sensor. Membrane 37, 37a, 37b and 37c can be formed having any suitable thickness to prevent debris or liquid from entering pump housing 31 and to avoid interference with peristaltic tube 23 and/or engagement of finger plates 4 therewith. For purpose of illustration and not limitation, as embodied herein, membrane 37, 37a, 37b and 37c can have a thickness of 0.33 mm.

Figure 12A:
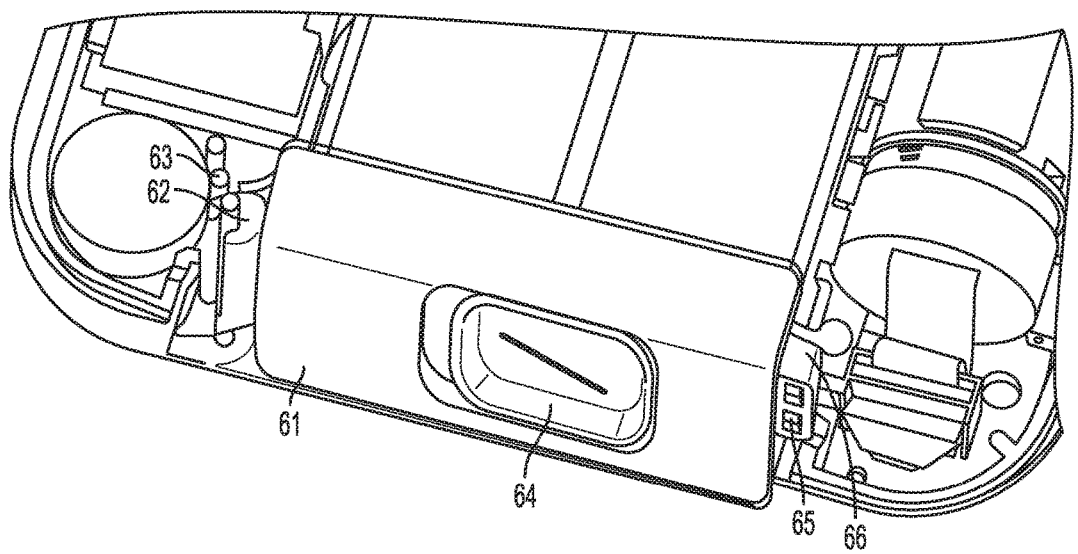
FIG. 12A is a top perspective view of an exemplary battery cover door of the pump of FIG. 1, with the battery cover door in a closed position, and selected portions cut away for purpose of illustration.
Figure 12B:
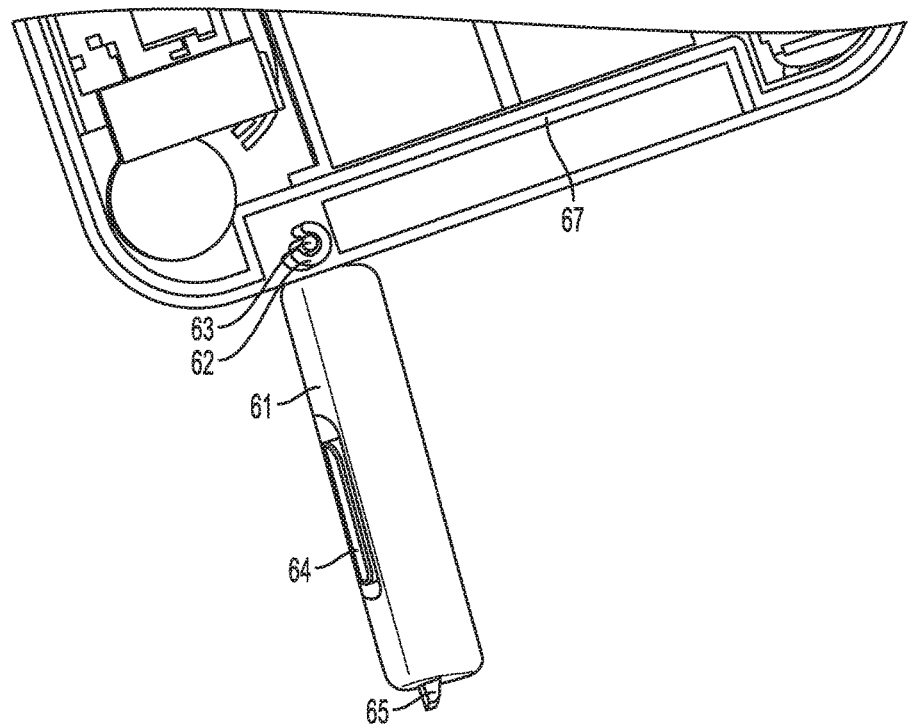
FIG. 12B is a top view of the exemplary battery cover door of FIG. 12A, with the battery cover door in an open position, and selected portions cut away for purpose of illustration.

Referring now to FIGS. 12A-12B, for the purpose of illustration and not limitation, in some embodiments, the pump housing 31 can include a battery cover 611. The battery cover 61 can have a rectangular shape defining a length and width. In some embodiments, the battery cover 61 can be hingedly connected to the pump housing 31 along the width (referred to as a "barn door arrangement"). In alternative embodiments battery cover 61 can be hingedly connected to the pump housing 31 along the length (referred to as a "tailgate arrangement"). FIGS. 12A-12B show the battery cover 61 in the barn door arrangement. As embodied herein, the pump housing 31 can include a rod 63. The battery cover 61 can include a hinge 62 having a 'C' shape. The C-shaped hinge 62 can allow the battery cover 61 to snap off of the pump housing 31 if urged too far away from the pump housing 31 without damaging the hinge and allowing the battery cover 61 to be reinstalled. In this manner, preventing damage to the battery cover 61 from over extension of the battery cover can provide a benefit for a user with poor dexterity. Battery cover 61 can include a release button 64 coupled to a latch projection 65. Actuation of release button 64, for example by sliding release button away from latch projection 65, can release latch projection from a latch receptacle 66 in pump housing 31 to allow hinged movement of battery cover 61 away from pump housing 31. The battery compartment can also include a gasket to insulate the battery compartment and protect the battery compartment from fluid ingress.

Figure 13:
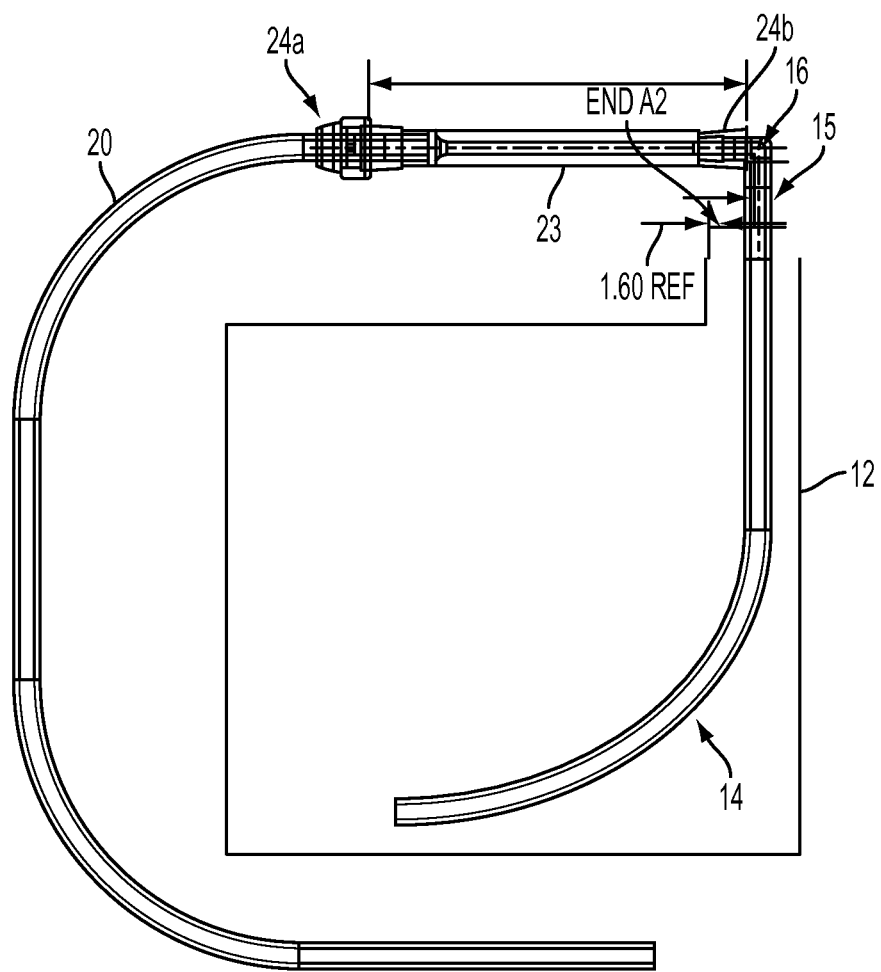
FIG. 13 is a plan view of an exemplary delivery tube assembly and fluid reservoir for use with the disclosed subject matter.

Referring now to FIG. 13, as embodied herein, cassette housing 11 can contain a fluid reservoir therein. For example, the housing itself can define the fluid reservoir, or an additional component to define the reservoir can be contained therein. If provided separately, the fluid reservoir 12 can be disposed in the cassette housing 11. For example, and as embodied herein, the cassette housing 11 can be configured with two enclosure clamshell portions 17 and 18 (as shown for example in FIGS. 1-3), which can receive and contain the fluid reservoir 12. The two clamshell portions 17 and 18 can be adhered or otherwise joined together, for example by ultrasonic welding.

As embodied herein, fluid reservoir 12 can include a flexible pouch, which can have any of a variety of suitable shapes. Opposing sides of the pouch can be secured about a perimeter to form the fluid reservoir 12, for example by thermal or radio frequency (RF) welding or the like. The fluid reservoir 12 can have a dip tube 14. The dip tube 14 can be configured, for example and without limitation, from SUNLITE VYSUN 102-80-26 (Non-DEHP PVC), DuPont Elvax 3182-2 EVA, or any suitable tubing material. As embodied herein, the dip tube 14 can have a length within a range of approximately 108-111 mm, with a plurality of approximately 2 mm diameter apertures disposed therein. The dip tube 14 can extend from the fluid reservoir 12 to serve as a delivery tube if desired or appropriate. Alternatively, and as embodied herein, an adaptor disposed external to the cassette housing 11 can be provided and coupled to a proximal end of the dip tube 14. In this manner, a separate delivery tube can be coupled to the adaptor for delivery of the beneficial agent from the fluid reservoir 12 to the user by operation of the pump 30. Additionally, a peristaltic tube can be provided between or as a part of the dip tube 14 and/or the delivery tube for interaction with the pump 30.

For the purpose of illustration and not limitation, an exemplary embodiment of such an adaptor is depicted in FIG. 13. As shown, the fluid reservoir 12 includes an adaptor 15 disposed external to the cassette housing 11. Adaptor 15 can be coupled to a proximal end of the dip tube 14. As embodied herein, a polypropylene-barbed elbow fitting 16 is provided at the proximal end of the dip tube 14. The elbow fitting 16 can be adhered to the exterior end of the dip tube 14 and oriented in plane with the fluid reservoir 12. A peristaltic tube 23 can be installed or coupled to an opposing end of the elbow fitting 16. For example, and as embodied herein, the peristaltic tube 23 can be formed from a section of Saint Gobain Biosil Precision tubing material. The peristaltic tube 23 can have an inside diameter of 1.6 mm and an outside diameter of 4.8 mm. A junction fitting 24 is joined to the peristaltic tube 23, and a delivery tube 20 can be adhered into the junction fitting 24. As such, the delivery tube 20 can be fluidly coupled with the fluid reservoir 12.

Each of the components described herein can be made of any suitable material (e.g., plastic, composites, metal, etc.) and technique for its intended purpose. In addition to the specific embodiments claimed below, the disclosed subject matter is also directed to other embodiments having any other possible combination of the dependent features claimed below and those disclosed above. As such, the particular features disclosed herein can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

The devices and techniques of the disclosed subject matter can be used for delivery of any of a variety of suitable fluid substances of corresponding volume or dose.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A device for delivering a beneficial agent, comprising:
    a cassette including a cassette housing with a fluid reservoir defined therein, the cassette housing having a cassette base region, the cassette base region including a back surface and a front surface opposite the back surface, the cassette base region including a boundary comprising an opening extending between and through the front surface and back surface of the cassette base region;
    a delivery tube fluidly coupled with the fluid reservoir;
    a pump including a pump housing containing a pump assembly having a fluid drive component, the pump housing having a receiving region to receive the cassette base region, the fluid drive component disposed proximate the receiving region; and
    a lock member coupled to the pump housing and movable between an open position and a closed position,
    wherein the cassette is configured so as to be capable of being inserted into and removed from the receiving region when the lock member is in the open position, and secured to the pump with the boundary of the cassette base region received by the receiving region with the lock member through the opening and a length of the delivery tube in operative engagement with the fluid drive component when the lock member is in the closed position.

2. The device of claim 1, further comprising an alignment pin operatively coupled to the lock member, wherein movement of the lock member between the open position and the closed position extends at least a portion of the alignment pin into engagement with the cassette housing.

3. The device of claim 2, wherein the cassette housing defines a receiving recess proximate the cassette base region to receive the alignment pin when the lock member is moved toward the closed position.

4. The device of claim 3, wherein the receiving recess is tapered toward a closed end.

5. The device of claim 3, wherein the receiving recess is defined by an alignment key projecting from a cassette body region into the cassette base region.

6. The device of claim 2, wherein the alignment pin comprises a tapered end.

7. The device of claim 2, wherein the lock member comprises a protrusion and the alignment pin comprises a notch to receive the protrusion to engage the lock member to operatively couple the alignment pin to the lock member.

8. The device of claim 1, wherein the receiving region further comprises a torsion spring mechanically coupled to the lock member.

9. The device of claim 1, wherein the lock member is a latch.

10. The device of claim 9, wherein the latch further comprises a latch cam surface; and
the pump further comprises an occlusion block disposed proximate the receiving region and having an occlusion block cam surface, the occlusion block being biased to urge the occlusion block cam surface against the latch cam surface.

11. The device of claim 10, wherein the latch cam surface and the occlusion block cam surface are configured to urge the occlusion block toward an operative position to hold the peristaltic tube in functional relationship to the fluid drive component when the latch is moved from the open position toward the closed position.

12. The device of claim 11, wherein the latch cam surface and the occlusion block cam surface are configured to define a dead zone wherein the occlusion block remains in the operative position during continued movement of the latch from the open position to the closed position.

13. The device of claim 12, wherein the dead zone is defined by 10 degrees of final movement of the latch from the open position to the closed position.

14. The device of claim 9, wherein the latch comprises a pivotal latch mounted on a hinge.

15. The device of claim 9, wherein the latch comprises a draw latch mounted for sliding movement.

16. The device of claim 1, further comprising a beneficial agent contained in the fluid reservoir.

17. The device of claim 16, wherein the beneficial agent comprises one or more of levodopa and carbidopa.

18. The device of claim 1, wherein the cassette base region includes an engagement surface configured to be engaged by the lock member when in the closed position.

19. The device of claim 18, wherein the engagement surface comprises a recessed area recessed relative the back surface of the cassette base region.

20. The device of claim 19, wherein the recessed area is shaped to receive the lock member when in the closed position.

* * * * *